(12) United States Patent
Martin

(10) Patent No.: US 10,493,089 B2
(45) Date of Patent: Dec. 3, 2019

(54) SOLID COMPOSITION COMPRISING AMORPHOUS SOFOSBUVIR

(71) Applicant: Sandoz AG, Basel (CH)

(72) Inventor: Nolwenn Martin, Kundl/Tirol (AT)

(73) Assignee: Sandoz AG, Basel (CH)

( * ) Notice: Subject to any disclaimer, the term of this patent is extended or adjusted under 35 U.S.C. 154(b) by 195 days.

(21) Appl. No.: 15/129,149

(22) PCT Filed: Apr. 2, 2015

(86) PCT No.: PCT/EP2015/057411
§ 371 (c)(1),
(2) Date: Sep. 26, 2016

(87) PCT Pub. No.: WO2015/150561
PCT Pub. Date: Oct. 8, 2015

(65) Prior Publication Data
US 2017/0100422 A1 Apr. 13, 2017

(30) Foreign Application Priority Data

Apr. 3, 2014 (EP) ..................................... 14163434

(51) Int. Cl.
| | | |
|---|---|---|
| *A61K 31/7072* | (2006.01) | |
| *A61K 9/14* | (2006.01) | |
| *C07F 9/6558* | (2006.01) | |
| *C07H 19/10* | (2006.01) | |

(52) U.S. Cl.
CPC .......... *A61K 31/7072* (2013.01); *A61K 9/143* (2013.01); *A61K 9/146* (2013.01); *C07F 9/65586* (2013.01); *C07H 19/10* (2013.01)

(58) Field of Classification Search
None
See application file for complete search history.

(56) References Cited

U.S. PATENT DOCUMENTS

| | | | |
|---|---|---|---|
| 2002/0006951 A1* | 1/2002 | Hageman | A61K 9/0007 |
| | | | 514/406 |
| 2004/0134258 A1 | 7/2004 | Wang et al. | |
| 2010/0298257 A1 | 11/2010 | Ross et al. | |

FOREIGN PATENT DOCUMENTS

| | | |
|---|---|---|
| JP | 2012527477 A | 11/2012 |
| WO | 2010017965 A3 | 11/2010 |
| WO | 2010135569 A1 | 11/2010 |
| WO | 2011123645 A2 | 10/2011 |
| WO | 2013101550 A1 | 7/2013 |

OTHER PUBLICATIONS

Patel, V. I., & Dave, R. H. (2013). Evaluation of colloidal solid dispersions: physiochemical considerations and in vitro release profile . AAPS PharmSciTech, 14(2), 620-628. (Year: 2013).*
International Search Report and Written Opinion for PCT/EP2015/057411, dated Apr. 3, 2014, 16 pages.

* cited by examiner

*Primary Examiner* — Dale R Miller
(74) *Attorney, Agent, or Firm* — Luedeka Neely Group, P.C.

(57) ABSTRACT

A solid composition comprising sofosbuvir and at least one pharmaceutically acceptable matrix compound wherein at least 99 weight-% of the sofosbuvir comprised in the composition are present in amorphous form, at least 99 weight-% of the solid composition consist of the sofosbuvir and the at least one matrix compound, and wherein the solid composition contains the sofosbuvir in an amount of at least 55 weight-% based on the combined weight of the sofosbuvir and the at least one matrix compound.

20 Claims, 15 Drawing Sheets

SOLID COMPOSITION COMPRISING AMORPHOUS SOFOSBUVIR

Figure 1:
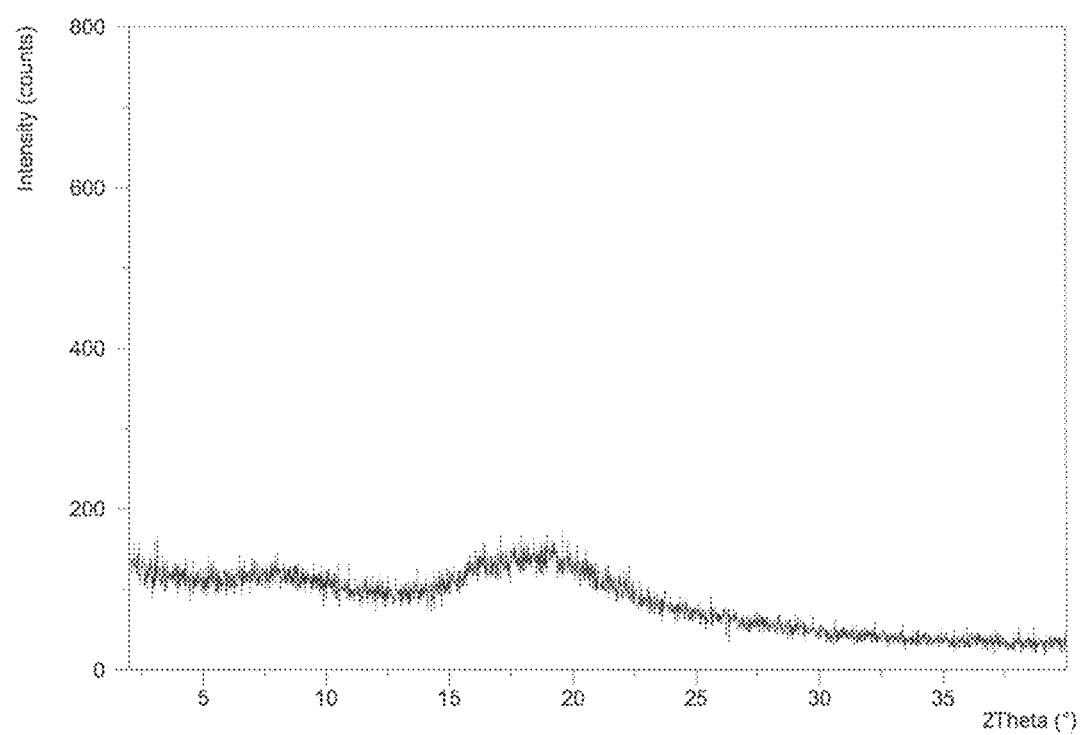

This application is a Section 371 national phase entry of PCT application PCT/EP2015/057411, filed Apr. 2, 2015. This application also claims the benefit of the earlier filing date of European patent application 14163434.5, filed Apr. 3, 2014.

The present invention relates to a solid composition comprising amorphous sofosbuvir and a process for the preparation of the solid composition. The present invention further relates to a pharmaceutical composition comprising the solid composition. Yet further, the present invention relates to the use of the solid composition and the pharmaceutical composition comprising the solid composition for the treatment of hepatitis C.

Sofosbuvir according to formula (I)

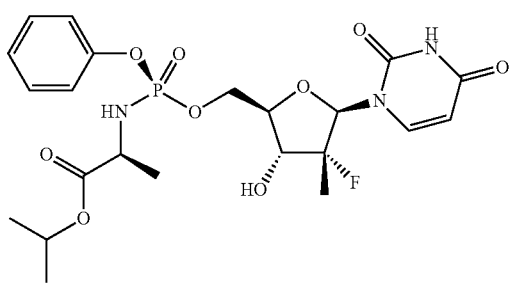

(I)

with IUPAC name (S)-isopropyl 2-(((S)-(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy) phosphoryl)amino)propanoate is a drug inhibiting the RNA polymerase used by the hepatitis C virus to replicate its RNA.

In WO 2010/135569 A, sofosbuvir is described as a moisture instable compound. In particular, it was found that under stress conditions at 40° C. and a relative humidity (RH) of 75%, sofosbuvir deliquesces after a few hours. Amorphous sofosbuvir, compared to its crystalline forms, is even less moisture stable and deliquesces at relative humidity above about 50%. On the other hand, compared to its crystalline forms, amorphous sofosbuvir is believed to show a higher solubility when applied to a patient.

Among many other drugs, WO 2013/101550 A describes sofosbuvir, referred to as PSI-7977. In particular, this document relates to a theoretical assessment tool allegedly useful to rank the intrinsic physical stability of amorphous drug substances. As parameter which indicates the physical stability, the crystallization tendency is mentioned. Without giving any details regarding the specific type of drug, WO 2013/101550 A discloses allegedly stable compositions which may contain from 1 to 50% by weight of the drug wherein, however, the drug content is preferably in the range of from 5 to 15% by weight. Not one single actual example directed to a concrete composition which would have been subjected to a respective stability test is disclosed in WO 2013/101550 A. Still further, theoretical examples according to WO 2013/101550 A directed to HCV inhibitors in general teach a very low drug content of only 10% by weight.

Therefore, the problem underlying the present invention is the provision of a stable composition comprising amorphous sofosbuvir which contains a high amount of the sofosbuvir.

Surprisingly, it was found that this problem can be solved if a solid composition is provided which contains the amorphous sofosbuvir and at least one pharmaceutically acceptable matrix compound wherein the solid composition essentially consists of the amorphous sofosbuvir and the at least one pharmaceutically acceptable matrix compound.

Therefore, the present invention relates to a solid composition comprising sofosbuvir according to formula (I)

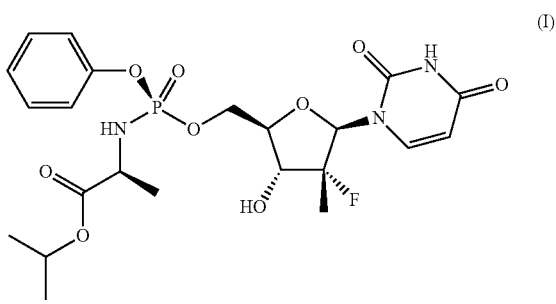 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

(I)

and at least one pharmaceutically acceptable matrix compound wherein at least 99 weight-% of the sofosbuvir comprised in the composition are present in amorphous form, at least 99 weight-% of the solid composition consist of the sofosbuvir and the at least one matrix compound, and wherein the solid composition contains the sofosbuvir in an amount of at least 55 weight-% based on the combined weight of the sofosbuvir and the at least one matrix compound.

Further, the present invention relates to a process for the preparation of a solid composition, comprising sofosbuvir according to formula (I)

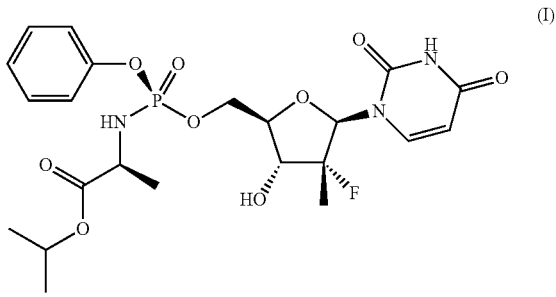 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

(I)

and at least one pharmaceutically acceptable matrix compound, wherein said process comprises embedding sofosbuvir in a matrix consisting of the at least one pharmaceutically acceptable matrix compound, starting from a solution of the sofosbuvir in at least one solvent, wherein the weight ratio of the sofosbuvir relative to the at least one matrix compound is at least 5.5:4.5.

The Solid Composition

Preferably, the solid composition according to the present invention contains the sofosbuvir in an amount in the range of from 55 to 95 weight-%, more preferably in the range of from 55 to 92 weight-%, based on the combined weight of the sofosbuvir and the at least one matrix compound. More preferably, the solid composition contains the sofosbuvir in an amount in the range of from 55 to 90 weight-%, more preferably from 60 to 85 weight-%, more preferably from 70 to 80 weight-%, based on the combined weight of the sofosbuvir and the at least one matrix compound. Preferred ranges of the sofosbuvir content of the solid compositions are from 70 to 74 weight-% or from 72 to 76 weight-% or from 74 to 78 weight-% or from 76 to 80 weight-%, based on the combined weight of the sofosbuvir and the at least one matrix compound. A preferred range is also from 74 to 76 weight-%.

Compared to the teaching of the prior art, in particular the teaching of WO 2013/101550 A, the present invention thus provides the possibility to provide compositions having a high sofosbuvir content which allow to administer the sofosbuvir to a patient in need thereof with only a few or even only one dosage. Further in particular with regard to dosage forms such as tablets, these high sofosbuvir contents allow to prepare smaller tablets which can be swallowed easily by the patient.

According to the present invention, at least 99 weight-% of the sofosbuvir comprised in the composition are present in amorphous form. Preferably, at least 99.5 weight-%, more preferably at least 99.6 weight-%, more preferably at least 99.7 weight-%, more preferably at least 99.8 weight-%, more preferably at least 99.9 weight-% of the sofosbuvir comprised in the composition are present in amorphous form. More preferably, at least 99.95 weight-%, more preferably at least 99.99 weight-% of the sofosbuvir comprised in the composition are present in amorphous form. The term "amorphous form" as used in this context of the present invention relates to sofosbuvir which, subjected to X-ray powder diffraction spectroscopy, does not contain any detectable crystalline form.

According to the present invention, at least 99 weight-% of the solid composition consist of the sofosbuvir and the at least one matrix compound. Preferably, at least 99.5 weight-%, more preferably at least 99.6 weight-%, more preferably at least 99.7 weight-%, more preferably at least 99.8 weight-%, more preferably at least 99.9 weight-% of the solid composition consist of the sofosbuvir and the at least one matrix compound. More preferably, at least 99.95 weight-%, more preferably at least 99.99 weight-% of the solid composition consist of the sofosbuvir and the at least one matrix compound.

Certain compositions disclosed in WO 2013/101550 A which may be regarded as examples and which describe compositions comprising 10% by weight of a drug different from sofosbuvir contain, in addition to the drug and the matrix material copovidone, a surfactant, namely vitamin E TPGS, sorbitan monolaurate, propylene glycol monocarpylate, or a combination of vitamin E TGPS and lauryl glycol FCC. These surfactants are disclosed to be present in the compositions in very significant amounts of 7 weight-%, based on the total weight of the compositions. Thus, it appears that WO 2013/101550 A, in its most concrete embodiments, teaches the mandatory use of surfactants in significant amounts if a physically stable composition is to be provided. Surprisingly, for the solid compositions of the present invention comprising at least 55 weight-% of sofosbuvir, it was found that no such surfactant is necessary to provide a physically stable composition. Therefore, the present invention also relates to the above-described solid composition, comprising less than 0.1 weight-%, preferably less than 0.01 weight-%, more preferably less than 0.001 weight-%, more preferably less than 0.0001 weight-%, more preferably in the range of from 0 to 0.00001 weight-% of vitamin E TPGS (D-alpha-tocopheryl polyethylene glycol 1000 succinate), or of sorbitan monolaurate, or of a combination of vitamin E TGPS and lauryl glycol FCC. Preferably, the present invention relates to the above-described solid composition, comprising less than 0.1 weight-%, preferably less than 0.01 weight-%, more preferably less than 0.001 weight-%, more preferably less than 0.0001 weight-%, more preferably less than 0.00001 weight-%, more preferably in the range of from 0 to 0.00001 weight-% of polysorbate 20, or of polysorbate 40, or of polysorbate 60, or of polysorbate 80, or of Cremophor RH 40, or of Cremophor EL, or of Gelucire 44/14, or of Gelucire 50/13, or of vitamin E TPGS, or of propylene glycol laurate, or of sodium lauryl sulfate, or of sorbitan monolaurate, or of a combination or a mixture of two or more thereof. More preferably, the present invention relates to the above-described solid composition, comprising less than 0.1 weight-%, preferably less than 0.01 weight-%, more preferably less than 0.001 weight-%, more preferably less than 0.0001 weight-%, more preferably in the range of from 0 to 0.00001 weight-% of polyoxyethylene castor oil derivatives, e.g. polyoxyethyleneglycerol triricinoleate or polyoxyl 35 castor oil (Cremophor EL; BASF Corp.) or polyoxyethyleneglycerol oxystearate such as polyethylenglycol 40 hydrogenated castor oil (Cremophor RH 40, also known as polyoxyl 40 hydrogenated castor oil or macrogolglycerol hydroxystearate) or polyethylenglycol 60 hydrogenated castor oil (Cremophor RH 60); or a mono fatty acid ester of polyoxyethylene sorbitan, such as a mono fatty acid ester of polyoxyethylene (20) sorbitan, e.g. polyoxyethylene (20) sorbitan monooleate (Tween 80), polyoxyethylene (20) sorbitan monostearate (Tween 60), polyoxyethylene (20) sorbitan monopalmitate (Tween 40), or polyoxyethylene (20) sorbitan monolaurate (Tween 20), or polyoxyethylene alkyl ethers, e.g. polyoxyethylene (3) lauryl ether, polyoxyethylene (5) cetyl ether, polyoxyethylene (2) stearyl ether, polyoxyethylene (5) stearyl ether; or polyoxyethylene alkylaryl ethers, e.g. polyoxyethylene (2) nonylphenyl ether, polyoxyethylene (3) nonylphenyl ether, polyoxyethylene (4) nonylphenyl ether, polyoxyethylene (3) octylphenyl ether; or polyethylene glycol fatty acid esters, e.g. PEG-200 monolaurate, PEG-200 dilaurate, PEG-300 dilaurate, PEG-400 dilaurate, PEG-300 distearate, PEG-300 dioleate; alkylene glycol fatty acid mono esters, e.g. propylene glycol monolaurate (lauroglycol, such as lauroglycol FCC); or sucrose fatty acid esters, e.g. sucrose monostearate, sucrose distearate, sucrose monolaurate, sucrose dilaurate; or sorbitan fatty acid mono esters such as sorbitan mono laurate (Span 20), sorbitan monooleate, sorbitan monopalmitate (Span 40), or sorbitan stearate; or D-alpha-tocopheryl polyethylene glycol 1000 succinate; or a combination or mixture thereof; or block copolymers of ethylene oxide and propylene oxide, also known as polyoxyethylene polyoxypropylene block copolymers or polyoxyethylene polypropyleneglycol, such as Poloxamer 124, Poloxamer 188, Poloxamer 237, Poloxamer 388, or Poloxamer 407, or a combination of two or more thereof. More preferably, the present invention relates to the above-described solid composition, comprising less than 0.1 weight-%, preferably less than 0.01 weight-%, more preferably less than 0.001 weight-%, more preferably less than 0.0001 weight-%, more preferably in the range of from 0 to 0.00001 weight-% of a pharmaceutically acceptable surfactant having an HLB value of from 2-20. More preferably, the present invention relates to the above-described solid composition, comprising less than 0.1 weight-%, preferably less than 0.01 weight-%, more preferably less than 0.001 weight-%, more preferably less than 0.0001 weight-%, more preferably in the range of from 0 to 0.00001 weight-% of a pharmaceutically acceptable non-ionic surfactant. More preferably, the present invention relates to the above-described solid composition, comprising less than 0.1 weight-%, preferably less than 0.01 weight-%, more preferably less than 0.001 weight-%, more preferably less than 0.0001 weight-%, more preferably in the range of from 0 to 0.00001 weight-% of a pharmaceutically acceptable surfactant. In each case, the weight-% values are based on the total weight of the solid composition.

Regarding the at least one pharmaceutically acceptable matrix compound, it was surprisingly found that matrix compounds which exhibit specific characteristics when subjected to a dynamic vapor sorption measurement are especially suitable as matrix compounds according to the present invention. In particular, it was found that these matrix compounds can stabilize amorphous sofosbuvir in the solid compositions according to the present invention even at high sofosbuvir contents, such as sofosbuvir contents in the range of from 55 to 95 weight-%, preferably in the range of from 55 to 92 weight-%, more preferably in the range of from 55 to 90 weight-%, more preferably in the range of from 60 to 85 weight-%, more preferably in the range of from 70 to 80 weight-%. Thus, although at such high sofosbuvir contents, the respective amount of matrix compound contained in the solid composition is necessarily low, the matrix compounds exhibiting specific characteristics when subjected to a dynamic vapor sorption measurement can stabilize the sofosbuvir in its amorphous form. Hence, it was surprisingly found that although the sofosbuvir content of the preferred solid compositions of the present invention is significantly higher than those taught in the art, thus having a significantly lower content of stabilizing matrix compounds, in particular the preferred matrix compounds described above allow to provide stable solid compositions which, even at stress conditions, in particular at 75% relative humidity at 40° C., do not deliquesce. Still further, it was found that the amorphous sofosbuvir comprised in the solid compositions of the present invention does not show any tendency to crystallize in the solid compositions according to the present invention.

Therefore, the present invention relates to the solid compositions described above, having a moisture stability of at least 95%, preferably at least 98%, more preferably at least 99%, wherein the moisture stability is defined as the amount of solid amorphous sofosbuvir which is present in the solid composition after having been exposed to a relative humidity of 75% at 40° C. for 8 weeks, relative to the amount of solid amorphous sofosbuvir which is present in the solid composition before said exposure. The term "before said exposure" as used in this context of the present application relates to a solid composition which, prior to being exposed to a relative humidity of 75% at 40° C., has been stored, directly after its preparation, at a relative humidity of 30% at 25° C. Therefore, the present invention also relates to the solid compositions described above, having a moisture stability of at least 95%, preferably at least 98%, more preferably at least 99%, wherein the moisture stability is defined as the amount of solid amorphous sofosbuvir which is present in the solid composition after having been exposed to a relative humidity of 75% at 40° C. for 8 weeks, relative to the amount of solid amorphous sofosbuvir which is present in the solid composition when, directly after its preparation, being stored at a relative humidity of 30% at 25° C.

Regarding the specific characteristics of the preferred matrix compounds according to the present invention when subjected to a dynamic vapor sorption measurement, it was found that in the adsorption-desorption isotherms of these matrix compounds, the mass difference $\Delta m(desorption)$ at 75% relative humidity and 25° C. is greater than or equal to the mass difference $\Delta m(adsorption)$ at 75% relative humidity and 25° C. Even more preferably, the mass difference $\Delta m(desorption)$ at 75% relative humidity and 25° C. is greater than the mass difference $\Delta m(adsorption)$ at 75% relative humidity and 25° C. Without wanting to be bound by any theory, it is believed that the specific pore properties and/or the specific surface properties, either regarding the respective chemical and/or the physical nature thereof, of the preferred matrix compounds may lead to their specific and advantageous suitability for stabilizing the amorphous sofosbuvir in the solid composition, even at such low matrix compound contents of the solid compositions. Regarding the dynamic vapor sorption measurements and the determination of the values of $\Delta m(desorption)$ and $\Delta m(adsorption)$ at 75% relative humidity and 25° C., specific reference is made to Reference Example 4 of the present invention.

Therefore, the present invention relates to a solid composition comprising sofosbuvir according to formula (I)

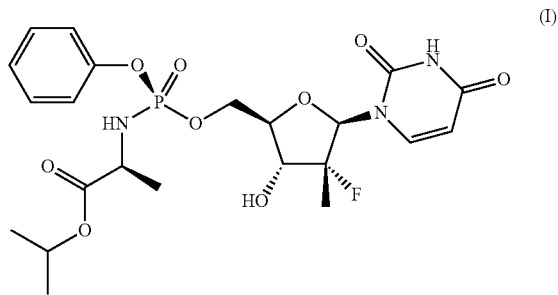 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

(I)

and at least one pharmaceutically acceptable matrix compound wherein at least 99 weight-% of the sofosbuvir comprised in the composition are present in amorphous form, at least 99 weight-% of the solid composition consist of the sofosbuvir and the at least one matrix compound, and wherein the solid composition contains the sofosbuvir in an amount of at least 55 weight-%, preferably in the range of from 55 to 90 weight-%, preferably from 60 to 85 weight-%, more preferably from 70 to 80 weight-%, based on the combined weight of the sofosbuvir and the at least one matrix compound, and wherein in the adsorption-desorption isotherms of the at least one matrix compound, the mass difference $\Delta m(desorption)$ at 75% relative humidity and 25° C. is greater than or equal to, preferably greater than, the mass difference $\Delta m(adsorption)$ at 75% relative humidity and 25° C.

Regarding the at least one pharmaceutically acceptable matrix compound, it was found that in particular hydrophilic polymers, preferably hydrophilic water-soluble polymers, and silicon-based inorganic adsorbents are suitable matrix compounds. Preferably, the at least one matrix compound is selected from the group consisting of hydrophilic water-soluble polymers, silicon-based inorganic adsorbents and a combination of two or more thereof. For example, the at least one matrix compound is selected from the group consisting of hydrophilic polymers, preferably hydrophilic water-soluble polymers, and combinations of two or more thereof; or from the group consisting of silicon-based inorganic adsorbents and combinations of two or more thereof; or from the group consisting of combinations of at least one hydrophilic polymer, preferably hydrophilic water-soluble polymer, and at least one silicon-based inorganic adsorbent.

Examples of hydrophilic polymers include, but are not restricted to, polysaccharides, preferably cellulose derivatives, polyvinylpyrrolidones, polyethylene glycols, polyethylene glycol based copolymers, polyacrylic acids, salts of polyacrylic acids, polyvinyl alcohols, polyacrylamide copolymers, methacrylic acid copolymers, methacrylate copolymers, pectines, chitin derivatives, chitosan derivatives, polyphosphates, polyoxazolines, and mixtures of two or more thereof. More specific examples of hydrophilic polymers include, but are not restricted to, cellulose derivatives selected from the group consisting of alkylcellulose, preferably methylcellulose, ethylcellulose, or propylcellulose; hydroxyalkylcellulose, preferably hydroxymethylcellulose, hydroxyethylcellulose, or hydroxypropylcellulose; hydroxyalkylalkylcellulose, preferably hydroxyethylmethylcellulose (HEMC), or hydroxypropylmethylcellulose (HPMC); carboxyalkylcellulose, preferably carboxymethylcellulose (CMC), carboxymethylhydroxyethylcellulose (CMHEC), hydroxyethylcarboxymethylcellulose (HECMC); sodium carboxymethylcellulose, cellulose acetate phthalate (CAP), hydroxypropylmethylcellulose acetate (HPMCA), hydroxypropylmethylcellulose phthalate (HPMCP), hydroxypropylmethylcellulose acetate succinate (HPMCAS), and a mixture of two or more thereof.

Examples of silicon-based inorganic adsorbents include, but are not restricted to, silica, silicates, and a combination of two or more thereof. For example, the silicon-based inorganic adsorbent is selected from the group consisting of silicas and combinations of two or more thereof; or from the group consisting of silicates and combinations of two or more thereof; or from the group consisting of at least one silica and at least one silicate. The term "silicate" as used in this context of the present invention refers to naturally occurring or synthesized compounds containing an anionic silicon compound, preferably an oxide. Examples of such silicates include, but are not restricted to, nesosilicates comprising the structure unit $[SiO_4]^{4-}$, sorosilicates comprising the structure unit $[Si_2O_7]^{6-}$, cyclosilicates comprising the structure unit $[Si_nO_{3n}]^{2n-}$, single chain inosilicates comprising the structure unit $[Si_nO_{3n}]^{2n-}$, double chain inosilicates comprising the structure unit $[Si_{4n}O_{11n}]^{6n-}$, phyllosilicates comprising the structure unit $[Si_nO_{5n}]^{2n-}$, or tectosilicates with a 3D framework comprising the structure unit $[Al_xSi_yO_{2(x+y)}]^{x-}$. The term "silica" as used in this context of the present invention refers to naturally occurring or synthesized silica. Examples of such silica include, but are not restricted to, fumed silica, precipitated silica, gel silica, colloidal silica.

Surprisingly, it was found that silicon-based inorganic adsorbents are preferred which have a pH in a defined range, preferably a pH of at least 6.0. More preferably, the at least one matrix compound has a pH in the range of from 6.0 to 9.0, more preferably in the range of from 6.5 to 8.5, more preferably in the range of from 7.0 to 8.0. Regarding the pH of the silicon-based inorganic adsorbents and its determination, reference is made to Reference Example 1 of the present invention.

Generally, it is conceivable that the solid composition of the present invention contains at least one silicon-based inorganic adsorbent having a pH in the above-defined preferred ranges and at least one silicon-based inorganic adsorbent having a pH outside these ranges. Preferably, all silicon-based inorganic adsorbents comprised in the solid composition of the present invention have a pH in the above-defined preferred ranges.

As described above, the solid composition according to the present invention comprises at least one hydrophilic, preferably water-soluble, polymer and/or at least one silicon-based inorganic adsorbent. Generally, it is possible that the solid composition contains at least one hydrophilic, preferably water-soluble, polymer and at least one silicon-based inorganic adsorbent. Preferably, the solid composition of the present invention comprises either at least one hydrophilic, preferably water-soluble, polymer or at least one silicon-based inorganic adsorbent. Preferably, the solid composition of the present invention comprises, as matrix compound, one, two, or three, preferably one or two, more preferably one hydrophilic, preferably water-soluble, polymer(s). Preferably, the solid composition of the present invention comprises, as matrix compound, one, two, or three, preferably one or two, more preferably one silicon-based inorganic adsorbent(s).

FIRST PREFERRED EMBODIMENT

Therefore, according to a first preferred embodiment of the present invention, the at least one matrix compound comprises at least one silicon-based inorganic adsorbent, preferably consists of at least one, more preferably one silicon-based inorganic adsorbent.

Therefore, the present invention also relates to a solid composition comprising sofosbuvir according to formula (I) and at least one pharmaceutically acceptable matrix compound wherein at least 99 weight-% of the sofosbuvir comprised in the composition are present in amorphous form, at least 99 weight-% of the solid composition consist of the sofosbuvir and the at least one matrix compound, and wherein the solid composition contains the sofosbuvir in an amount of at least 55 weight-% based on the combined weight of the sofosbuvir and the at least one matrix compound, wherein the at least one matrix compound comprises at least one silicon-based inorganic adsorbent, preferably consists of at least one, more preferably one silicon-based inorganic adsorbent wherein in the adsorption-desorption isotherm of the silicon-based inorganic adsorbent, the mass difference Δm(desorption) at 75% relative humidity and 25° C. is greater than or equal to, preferably greater than, the mass difference Δm(adsorption) at 75% relative humidity and 25° C., determined according to dynamic vapor sorption measurement.

Also, the present invention also relates to a solid composition comprising sofosbuvir according to formula (I) and at least one pharmaceutically acceptable matrix compound wherein at least 99 weight-% of the sofosbuvir comprised in the composition are present in amorphous form, at least 99 weight-% of the solid composition consist of the sofosbuvir and the at least one matrix compound, and wherein the solid composition contains the sofosbuvir in an amount of at least 55 weight-% based on the combined weight of the sofosbuvir and the at least one matrix compound, wherein the at least one matrix compound comprises at least one silicon-based inorganic adsorbent, preferably consists of at least one, more preferably one silicon-based inorganic adsorbent wherein in the adsorption-desorption isotherm of the silicon-based inorganic adsorbent, the mass difference Δm(desorption) at 75% relative humidity and 25° C. is greater than or equal to, preferably greater than, the mass difference Δm(adsorption) at 75% relative humidity and 25° C., determined according to dynamic vapor sorption measurement, and wherein the pH of the silicon-based inorganic adsorbent is in the range of from 6.0 to 9.0, preferably in the range of from 6.5 to 8.5, more preferably in the range of from 7.0 to 8.0.

Preferably, the oil adsorbance of the at least one silicon-based inorganic adsorbent is in the range of from 1.0 to 5.0 mug, preferably in the range of from 1.3 to 4.5 ml/g, more preferably in the range of from 1.5 to 4.0 mug. Generally, it is conceivable that the solid composition of the present invention contains at least one silicon-based inorganic adsorbent having an oil adsorbance in the above-defined preferred ranges and at least one silicon-based inorganic adsorbent having an oil adsorbance outside these ranges. Preferably, all silicon-based inorganic adsorbents comprised in the solid composition of the present invention have an oil adsorbance in the above-defined preferred ranges.

Preferably, the bulk density of the at least one silicon-based inorganic adsorbent is in the range of from 10 to 500 g/ml, preferably in the range of from 30 to 400 g/ml, more preferably in the range of from 50 to 300 g/ml. Generally, it is conceivable that the solid composition of the present invention contains at least one silicon-based inorganic adsorbent having a bulk density in the above-defined preferred ranges and at least one silicon-based inorganic adsorbent having a bulk density outside these ranges. Preferably, all silicon-based inorganic adsorbents comprised in the solid composition of the present invention have having a bulk density in the above-defined preferred ranges.

Preferably, the silica is selected from the group consisting of fumed silica, precipitated silica, gel silica, colloidal silica, and a combination of two or more thereof, such as a combination of fumed silica and precipitated silica or a combination of fumed silica and colloidal silica or a combination of fumed silica and gel silica or a combination of precipitated silica and gel silica or a combination of precipitated silica and colloidal silica or a combination of gel silica and colloidal silica or a combination of fumed silica and precipitated silica and gel silica or a combination or fumed silica and gel silica and colloidal silica or a combination of precipitated silica and gel silica and colloidal silica or a combination of fumed silica and precipitated silica and gel silica and colloidal silica. Preferred silica include, but are not restricted to, the commercially available compounds Syloid® 72 FP, Syloid® 244 FP, both from Grace.

Preferably, the silicate is an aluminosilicate which, more preferably, additionally contains at least one alkali metal element selected from the group consisting of Li, Na, K, Rb, Cs and a combination of two or more thereof, preferably from the group consisting of Li, Na, K, and a combination of two or more thereof, more preferably from the group consisting of Na, K, and a combination of two or more thereof, and/or at least one alkaline earth metal element selected from the group consisting of Mg, Ca, Sr, Ba, and a combination of two or more thereof, preferably from the group consisting of Mg, Ca, Ba, and a combination of two or more thereof, preferably from the group consisting of Mg, Ca, and a combination of two or more thereof. More preferably, the silicate is an aluminosilicate which additionally contains at least one alkaline earth metal element selected from the group consisting of Mg, Ca, Sr, Ba, and a combination of two or more thereof, preferably from the group consisting of Mg, Ca, Ba, and a combination of two or more thereof, preferably from the group consisting of Mg, Ca, and a combination of two or more thereof. More preferably, the silicate is an aluminosilicate which additionally contains Mg. Preferred silicates include, but are not restricted to, the commercially available compounds Neusilin® UFL2, Neusilin® US2, both from Fuji Chemical Industry Co., Ltd.

Therefore, the present invention also relates to the solid composition as described above, wherein the at least one silicon-based inorganic adsorbent is selected from the group consisting of silica, silicates, and a combination of two or more thereof, wherein the silica is preferably selected from the group consisting of fumed silica, precipitated silica, gel silica, colloidal silica, and a combination of two or more thereof, and wherein the silicates are preferably aluminosilicates preferably comprising at least one alkali metal element and/or at least one alkaline earth metal element, more preferably at least one alkaline earth metal element, more preferably magnesium.

Generally, the silica and/or the silicate can be present in crystalline or amorphous form. Preferably, at least 90 weight-%, more preferably at least 95 weight-%, more preferably at least 99 weight-% of the at least one silicon-based inorganic adsorbent are present in amorphous form. More preferably, at least 99.5 weight-%, more preferably at least 99.9 weight-%, more preferably at least 99.99 weight-% of the at least one silicon-based inorganic adsorbent are present in amorphous form.

SECOND PREFERRED EMBODIMENT

According to a second preferred embodiment of the present invention, the at least one matrix compound comprises at least one hydrophilic, preferably water-soluble, polymer, preferably consists of at least one, more preferably one, hydrophilic, preferably water-soluble, polymer.

Therefore, the present invention also relates to a solid composition comprising sofosbuvir according to formula (I) and at least one pharmaceutically acceptable matrix compound wherein at least 99 weight-% of the sofosbuvir comprised in the composition are present in amorphous form, at least 99 weight-% of the solid composition consist of the sofosbuvir and the at least one matrix compound, and wherein the solid composition contains the sofosbuvir in an amount of at least 55 weight-% based on the combined weight of the sofosbuvir and the at least one matrix compound, wherein the at least one matrix compound comprises, preferably consists of, a hydrophilic, preferably water-soluble, polymer wherein in the adsorption-desorption isotherm of the hydrophilic, preferably water-soluble, polymer, the mass difference Δm(desorption) at 75% relative humidity and 25° C. is greater than or equal to, preferably greater than, the mass difference Δm(adsorption) at 75% relative humidity and 25° C., determined according to dynamic vapor sorption measurement.

Preferably, the at least one hydrophilic, preferably water-soluble, polymer has a solubility in water of at least 10 g/l, more preferably of at least 15 g/l, more preferably of at least 20 g/l, more preferably of at least 25 g/l, more preferably of at least 30 g/l, in each case at 23° C. at atmospheric pressure.

Examples of hydrophilic, preferably water-soluble, polymers include, but are not restricted to, polysaccharides, preferably cellulose derivatives, polyvinylpyrrolidones, polyethylene glycols, polyethylene glycol based copolymers, polyacrylic acids, salts of polyacrylic acids, polyvinyl alcohols, polyacrylamide copolymers, methacrylic acid copolymers, methacrylate copolymers, pectines, chitin derivatives, chitosan derivatives, polyphosphates, polyoxazolines, and mixtures or combinations of two or more thereof.

With regard to the chemical nature of the at least one hydrophilic, preferably water-soluble, polymer, polysaccharides and derivatives of polysaccharides are preferred. The polysaccharides can be homoglycans or heteroglycans. Further, the polysaccharides can be naturally occurring compounds or synthesized compounds. Regarding the derivatives of polysaccharides, compounds are preferred which are derivatized at one or more hydroxyl groups of the monosaccharide units of the polysaccharides. Polysaccharides and derivatives of polysaccharides include, but are not restricted to, cellulose and cellulose derivatives, such as alkylcellulose, such as methylcellulose, ethylcellulose, or propylcellulose; hydroxalkylcellulose, such as hydroxymethylcellulose, hydroxyethylcellulose, or hydroxypropylcellulose; hydroxyalkylalkylcellulose, such as hydroxyethylmethylcellulose (HEMC), or hydroxypropylmethylcellulose (HPMC); carboxyalkylcellulose, such as carboxymethylcellulose (CMC), carboxymethylhydroxyethylcellulose (CM-HEC), hydroxyethylcarboxymethylcellulose (HECMC); sodium carboxymethylcellulose, cellulose acetate phthalate (CAP), hydroxypropylmethylcellulose acetate (HPMCA), hydroxypropylmethylcellulose phthalate (HPMCP), hydroxypropylmethylcellulose acetate succinate (HPMCAS), and a mixture or combination of two or more thereof.

Preferably, the at least one hydrophilic, preferably water-soluble, polymer comprises, preferably consists of a cellulose derivative selected from the group consisting of hydroxyalkylalkylcelluloses and a mixture of two or more thereof. More preferably, the at least one hydrophilic, preferably water-soluble, polymer comprises, more preferably consists of, hydroxypropylmethylcellulose (HPMC).

Preferably, the weight average molecular weight ($M_w$) of the cellulose derivative, preferably the hydroxyalkylalkylcellulose, more preferably the hydroxypropylmethylcellulose, is in the range of from 7 to 225 kDa, more preferably in the range of from 7 to 100 kDa, more preferably in the range of from 7 to 30 kDa. According to the present invention, it is possible that the solid composition contains two or more cellulose derivative, preferably two or more hydroxyalkylalkylcelluloses, more preferably two or more hydroxypropylmethylcelluloses which differ only in the weight average molecular weight $M_w$.

Preferably, the molecular degree of substitution (DS) of the cellulose derivative, preferably the hydroxyalkylalkylcellulose, more preferably the hydroxypropylmethylcellulose, is in the range of from 0.3 to 2.8, more preferably in the range of from 0.6 to 2.5, more preferably in the range of from 1.0 to 2.3, more preferably in the range of from 1.3 to 2.0. According to the present invention, it is possible that the solid composition contains two or more cellulose derivative, preferably two or more hydroxyalkylalkylcelluloses, more preferably two or more hydroxypropylmethylcelluloses which differ only in the molecular degree of substitution. The parameter DS describes the number of hydroxyalkylalkylated sites per anhydroglucose unit of a given hydroxyalkylalkylcellulose.

Further according to the present invention, it is possible that the solid composition contains two or more cellulose derivatives, preferably two or more hydroxyalkylalkylcelluloses, more preferably two or more hydroxypropylmethylcelluloses which differ in the molecular degree of substitution and the weight average molecular weight $M_w$.

Also, the present invention also relates to a solid composition comprising sofosbuvir according to formula (I) and at least one pharmaceutically acceptable matrix compound wherein at least 99 weight-% of the sofosbuvir comprised in the composition are present in amorphous form, at least 99 weight-% of the solid composition consist of the sofosbuvir and the at least one matrix compound, and wherein the solid composition contains the sofosbuvir in an amount of at least 55 weight-% based on the combined weight of the sofosbuvir and the at least one matrix compound, wherein the at least one matrix compound comprises, preferably consists of, a cellulose derivative selected from the group consisting of hydroxyalkylalkylcelluloses and a mixture of two or more thereof, the cellulose derivative preferably comprising, more preferably consisting of, hydroxypropylmethylcellulose.

Further preferably, the present invention also relates to a solid composition comprising sofosbuvir according to formula (I) and at least one pharmaceutically acceptable matrix compound wherein at least 99 weight-% of the sofosbuvir comprised in the composition are present in amorphous form, at least 99 weight-% of the solid composition consist of the sofosbuvir and the at least one matrix compound, and wherein the solid composition contains the sofosbuvir in an amount of at least 55 weight-% based on the combined weight of the sofosbuvir and the at least one matrix compound, wherein the at least one matrix compound comprises at least one silicon-based inorganic adsorbent, preferably consists of at least one, more preferably one silicon-based inorganic adsorbent wherein in the adsorption-desorption isotherm of the silicon-based inorganic adsorbent, the mass difference Δm(desorption) at 75% relative humidity and 25° C. is greater than or equal to, preferably greater than, the mass difference Δm(adsorption) at 75% relative humidity and 25° C., determined according to dynamic vapor sorption measurement, said solid composition having a moisture stability of at least 95%, preferably at least 98%, more preferably at least 99%, wherein the moisture stability is defined as the amount of solid amorphous sofosbuvir which is present in the solid composition after having been exposed to a relative humidity of 75% at 40° C. for 8 weeks, relative to the amount of solid amorphous sofosbuvir which is present in the solid composition before said exposure.

Further preferably, the present invention relates to a solid composition comprising sofosbuvir according to formula (I) and at least one pharmaceutically acceptable matrix compound wherein at least 99 weight-% of the sofosbuvir comprised in the composition are present in amorphous form, at least 99 weight-% of the solid composition consist of the sofosbuvir and the at least one matrix compound, and wherein the solid composition contains the sofosbuvir in an amount of at least 55 weight-% based on the combined weight of the sofosbuvir and the at least one matrix compound, wherein the at least one matrix compound comprises, preferably consists of, a hydrophilic, preferably water-soluble, polymer, wherein in the adsorption-desorption isotherm of the hydrophilic, preferably water-soluble, polymer, the mass difference Δm(desorption) at 75% relative humidity and 25° C. is greater than or equal to, preferably greater than, the mass difference Δm(adsorption) at 75% relative humidity and 25° C., determined according to dynamic vapor sorption measurement, and wherein the hydrophilic, preferably water-soluble, polymer is selected from the group consisting of hydroxyalkylalkylcelluloses and a mixture of two or more thereof, the hydrophilic, preferably water-soluble, polymer preferably comprising, more preferably consisting of, hydroxypropylmethylcellulose, said solid composition having a moisture stability of at least 95%, preferably at least 98%, more preferably at least 99%, wherein the moisture stability is defined as the amount of solid amorphous sofosbuvir which is present in the solid composition after having been exposed to a relative humidity of 75% at 40° C. for 8 weeks, relative to the amount of solid amorphous sofosbuvir which is present in the solid composition before said exposure.

Preferably, the solid composition of the present invention is a solid dispersion. The term "solid dispersion" as used in this context of the present invention relates to a composition in a solid state, i.e. a state which is neither liquid nor gaseous, wherein the amorphous sofosbuvir is dispersed in at least one of the at least one pharmaceutically acceptable matrix compounds comprised in the solid dispersion, preferably in all of the at least pharmaceutically acceptable one matrix compounds comprised in the solid dispersion.

Preparation Process of the Solid Composition

The present invention also relates to the preparation of solid composition comprising amorphous sofosbuvir, in particular the solid composition described above.

Therefore, the present invention relates to a process for the preparation of a solid composition, comprising sofosbuvir according to formula (I)

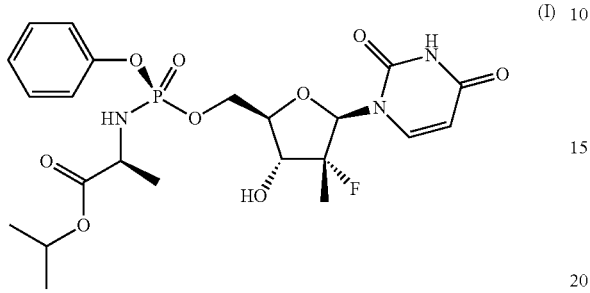

and at least one pharmaceutically acceptable matrix compound, preferably for the preparation of a solid composition as described herein, said process comprising embedding sofosbuvir in a matrix consisting of the at least one pharmaceutically acceptable matrix compound by melting the at least one pharmaceutically acceptable matrix compound in solid form together with the sofosbuvir in solid form, preferably by a hot-melt method, more preferably by a hot-melt extrusion method, wherein the weight ratio of the sofosbuvir relative to the at least one matrix compound is at least 5.5:4.5.

Therefore, the present invention relates to a process for the preparation of a solid composition, comprising sofosbuvir according to formula (I)

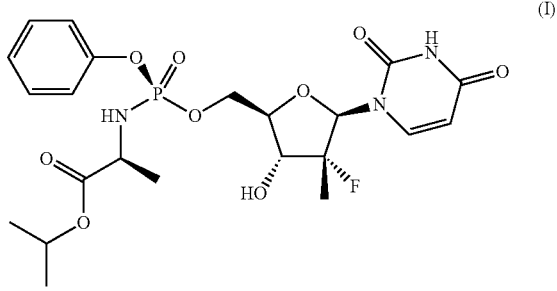 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

and at least one pharmaceutically acceptable matrix compound, preferably for the preparation of a solid composition as described herein, said process comprising embedding sofosbuvir in a matrix consisting of the at least one pharmaceutically acceptable matrix compound, starting from a solution of the sofosbuvir in at least one solvent, wherein the weight ratio of the sofosbuvir relative to the at least one matrix compound is at least 5.5:4.5.

According to the present invention, the solution of the sofosbuvir which is used as starting material for the preparation of the solid composition, can be prepared according to all conceivable means. For example, the solution can be prepared from amorphous sofosbuvir, from crystalline sofosbuvir which is present in one or more crystalline forms, from a sofosbuvir salt, from a sofosbuvir solvate, from a sofosbuvir hydrate, or from a combination of two or more thereof.

For example, it is possible to start from a solution prepared from crystalline sofosbuvir which is present in crystalline form 1. The preparation of crystalline form 1 of sofosbuvir is described, for example, in WO 2011/123645 A.

Further, it is possible to start from a solution prepared from amorphous sofosbuvir. Therefore, the present invention also relates to a process as described above, wherein the solution of the sofosbuvir in at least one solvent is prepared from sofosbuvir of which at least 95 weight-%, preferably at least 99 weight-%, more preferably at least 99.9 weight-% are present in its amorphous form.

No specific restrictions exist how the amorphous sofosbuvir is prepared. Generally, the amorphous sofosbuvir can be prepared from sofosbuvir which is present in at least one crystalline form or in amorphous form or as a mixture of at least one crystalline form and amorphous form. Preferably, the amorphous sofosbuvir is prepared from sofosbuvir of which at least 95 weight-%, preferably at least 99 weight-%, more preferably at least 99.9 weight-% are present in at least one crystalline form, such as in crystalline form 1. Generally, the crystalline and/or amorphous sofosbuvir is subjected to a melt method, preferably a hot-melt method, more preferably a hot-melt extrusion method from which the amorphous sofosbuvir is obtained, or is dissolved in at least one solvent, and the obtained solution is subjected to at least one treatment stage from which the amorphous sofosbuvir is obtained. Preferably, the crystalline and/or amorphous sofosbuvir, preferably the crystalline sofosbuvir, is dissolved in at least one solvent, and the obtained solution is subjected to at least one treatment stage from which the amorphous sofosbuvir is obtained. Regarding the at least one solvent, no specific restrictions exist. Preferably, the at least one solvent is selected from the group consisting of water, C1-C3 ketones, C1-C2 halogenated hydrocarbons, C1-C4 alcohols, C2-C6 ethers, C3-C5 esters, and a combination of two or more thereof, more preferably from the group consisting of water, C1-C4 alcohols, C1-C3 ketones, and a combination of two or more thereof, wherein more preferably, the at least one solvent comprises, more preferably consists of, water and C1-C4 alcohol, preferably water and ethanol, or comprises, more preferably consists of, acetone. Regarding the at least one treatment stage from which the amorphous sofosbuvir is obtained, no specific restrictions exist, provided that the amorphous sofosbuvir is obtained. Preferably, the treatment stage comprises subjecting at least a portion of the solution of the sofosbuvir to lyophilization or rapid-drying, preferably to rapid-drying, wherein the rapid-drying preferably comprises at least one atomization process, and is more preferably carried out by spray-drying or spray-granulation, preferably by spray-drying. Prior to the rapid-drying, the solution of the sofosbuvir can be concentrated with respect to the sofosbuvir content, for example by filtration, centrifugation, evaporation, adding sofosbuvir to the solution, or a combination of two or more of these methods.

Therefore, the present invention also relates to the process as described above, wherein the sofosbuvir is prepared by a method comprising (i) providing sofosbuvir in at least one crystalline form or in amorphous form or as a mixture of at least one crystalline form and amorphous form, preferably providing sofosbuvir of which at least 95 weight-%, preferably at least 99 weight-%, more preferably at least 99.9 weight-% are present in at least one crystalline form;

(ii) subjecting the sofosbuvir provided in (i) to a melt method, preferably a hot-melt method, more preferably a hot-melt extrusion method, obtaining the sofosbuvir of which at least 95 weight-%, preferably at least 99 weight-%, more preferably at least 99.9 weight-% are present in its amorphous form.

Therefore, the present invention also relates to the process as described above, wherein the sofosbuvir is prepared by a method comprising
(i) providing sofosbuvir in at least one crystalline form or in amorphous form or as a mixture of at least one crystalline form and amorphous form, preferably providing sofosbuvir of which at least 95 weight-%, preferably at least 99 weight-%, more preferably at least 99.9 weight-% are present in at least one crystalline form;
(ii) dissolving at least a portion of the sofosbuvir provided according to (i) in at least one solvent, obtaining a solution comprising the sofosbuvir;
(iii) subjecting at least a portion of the solution obtained according to (ii), optionally after concentrating, to lyophilization or rapid-drying, preferably rapid-drying, obtaining the sofosbuvir of which at least 95 weight-%, preferably at least 99 weight-%, more preferably at least 99.9 weight-% are present in its amorphous form.

The preferred rapid-drying method, the spray-drying, is not subjected to specific restrictions provided that the amorphous sofosbuvir is obtained. For example, the inlet temperature used may be in the range of from 50 to 100° C. For example, the outlet temperature used may be in the range of from 20 to 70° C.

Generally, the present invention also relates to a process for the preparation of sofosbuvir of which at least 95 weight-%, preferably at least 99 weight-%, more preferably at least 99.9 weight-% are present in its amorphous form, comprising
(i) providing sofosbuvir in at least one crystalline form or in amorphous form or as a mixture of at least one crystalline form and amorphous form, preferably providing sofosbuvir of which at least 95 weight-%, preferably at least 99 weight-%, more preferably at least 99.9 weight-% are present in at least one crystalline form;
(ii) dissolving at least a portion of the sofosbuvir provided according to (i) in at least one solvent, obtaining a solution comprising the sofosbuvir;
(iii) subjecting at least a portion of the solution obtained according to (ii), optionally after concentrating, to rapid-drying, obtaining the sofosbuvir of which at least 95 weight-%, preferably at least 99 weight-%, more preferably at least 99.9 weight-% are present in its amorphous form;
wherein the at least one solvent according to (ii) is preferably selected from the group consisting of water, C1-C3 ketones, C1-C2 halogenated hydrocarbons, C1-C4 alcohols, C2-C6 ethers, C3-C5 esters, and a combination of two or more thereof, more preferably from the group consisting of water, C1-C4 alcohols, C1-C3 ketones, and a combination of two or more thereof, wherein more preferably, the at least one solvent comprises, more preferably consists of, water and a C1-C4 alcohol, preferably water and ethanol, or comprises, more preferably consists of, acetone.

According to the present invention, solid compositions are preferably obtained of which at least 99 weight-% consist of the solid sofosbuvir and the at least one matrix compound. More preferably, solid compositions are obtained of which at least 99.5 weight-%, more preferably at least 99.6 weight-%, more preferably at least 99.7 weight-%, more preferably at least 99.8 weight-%, more preferably at least 99.9 weight-% consist of the sofosbuvir and the at least one matrix compound. More preferably, solid compositions are obtained of which at least 99.95 weight-%, more preferably at least 99.99 weight-% consist of the sofosbuvir and the at least one matrix compound.

Therefore, the present invention relates to a process for the preparation of a solid composition, comprising sofosbuvir according to formula (I)

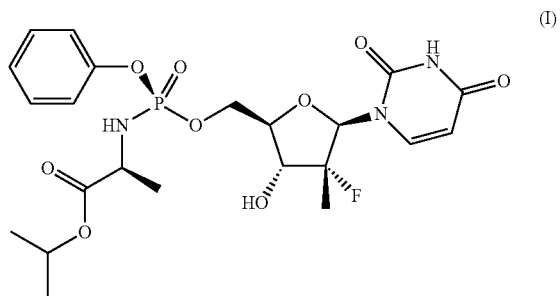 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

and at least one pharmaceutically acceptable matrix compound, preferably for the preparation of a solid composition as described above, said process comprising embedding sofosbuvir in a matrix consisting of the at least one pharmaceutically acceptable matrix compound by melting the at least one pharmaceutically acceptable matrix compound in solid form together with the sofosbuvir in solid form, preferably by a hot-melt method, more preferably by a hot-melt extrusion method, wherein the weight ratio of the sofosbuvir relative to the at least one matrix compound is at least 5.5:4.5, and wherein, in addition to the sofosbuvir and the at least one matrix compound, at most 1 weight-%, preferably at most 0.5 weight-%, more preferably at most 0.4 weight-%, more preferably at most 0.3 weight-%, more preferably at most 0.2 weight-%, more preferably at most 0.1 weight-%, more preferably at most 0.05 weight-%, more preferably at most 0.01 weight-% of compounds remaining in the solid composition after the preparation process and other than the solid sofosbuvir and the at least one matrix compound are used for the preparation of the solid composition, wherein said weight-% values are based on the total weight of the final solid composition obtained from the preparation process.

Therefore, the present invention relates to a process for the preparation of a solid composition, comprising sofosbuvir according to formula (I)

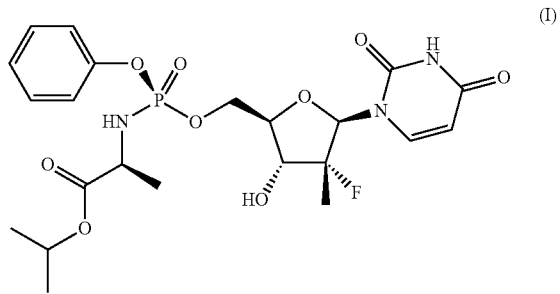 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

and at least one pharmaceutically acceptable matrix compound, preferably for the preparation of a solid composition as described above, said process comprising embedding sofosbuvir in a matrix consisting of the at least one pharmaceutically acceptable matrix compound, starting from a solution of the sofosbuvir in at least one solvent, wherein the weight ratio of the sofosbuvir relative to the at least one matrix compound is at least 5.5:4.5, and wherein, in addition to the sofosbuvir and the at least one matrix compound, at most 1 weight-%, preferably at most 0.5 weight-%, more preferably at most 0.4 weight-%, more preferably at most 0.3 weight-%, more preferably at most 0.2 weight-%, more preferably at most 0.1 weight-%, more preferably at most 0.05 weight-%, more preferably at most 0.01 weight-% of compounds remaining in the solid composition after the preparation process and other than the solid sofosbuvir and the at least one matrix compound are used for the preparation of the solid composition, wherein said weight-% values are based on the total weight of the final solid composition obtained from the preparation process.

Preferably, the present invention relates to the above-described process wherein, in addition to the sofosbuvir and the at least one matrix compound, less than 0.1 weight-%, preferably less than 0.01 weight-%, more preferably less than 0.001 weight-%, more preferably less than 0.0001 weight-%, more preferably in the range of from 0 to 0.00001 weight-% of vitamin E TPGS (D-alpha-tocopheryl polyethylene glycol 1000 succinate), or of sorbitan monolaurate, or of a combination of vitamin E TGPS and lauryl glycol FCC are employed for the preparation of the solid composition. Preferably, the present invention relates to the above-described process wherein, in addition to the solid sofosbuvir provided according to (i) and the at least one matrix compound employed in (ii), less than 0.1 weight-%, preferably less than 0.01 weight-%, more preferably less than 0.001 weight-%, more preferably less than 0.0001 weight-%, more preferably in the range of from 0 to 0.00001 weight-% of polysorbate 20, or of polysorbate 40, or of polysorbate 60, or of polysorbate 80, or of Cremophor RH 40, or of Cremophor EL, or of Gelucire 44/14, or of Gelucire 50/13, or of vitamin E TPGS, or of propylene glycol laurate, or of sodium lauryl sulfate, or of sorbitan monolaurate, or of a combination or a mixture of two or more thereof are employed for the preparation of the solid composition. More preferably, the present invention relates to the above-described process wherein, in addition to the solid sofosbuvir provided according to (i) and the at least one matrix compound employed in (ii), less than 0.1 weight-%, preferably less than 0.01 weight-%, more preferably less than 0.001 weight-%, more preferably less than 0.0001 weight-%, more preferably in the range of from 0 to 0.00001 weight-% of polyoxyethylene castor oil derivatives, e.g. polyoxyethyleneglycerol triricinoleate or polyoxyl 35 castor oil (Cremophor EL; BASF Corp.) or polyoxyethyleneglycerol oxystearate such as polyethylenglycol 40 hydrogenated castor oil (Cremophor RH 40, also known as polyoxyl 40 hydrogenated castor oil or macrogolglycerol hydroxystearate) or polyethylenglycol 60 hydrogenated castor oil (Cremophor RH 60); or a mono fatty acid ester of polyoxyethylene sorbitan, such as a mono fatty acid ester of polyoxyethylene (20) sorbitan, e.g. polyoxyethylene (20) sorbitan monooleate (Tween 80), polyoxyethylene (20) sorbitan monostearate (Tween 60), polyoxyethylene (20) sorbitan monopalmitate (Tween 40), or polyoxyethylene (20) sorbitan monolaurate (Tween 20), or polyoxyethylene alkyl ethers, e.g. polyoxyethylene (3) lauryl ether, polyoxyethylene (5) cetyl ether, polyoxyethylene (2) stearyl ether, polyoxyethylene (5) stearyl ether; or polyoxyethylene alkylaryl ethers, e.g. polyoxyethylene (2) nonylphenyl ether, polyoxyethylene (3) nonylphenyl ether, polyoxyethylene (4) nonylphenyl ether, polyoxyethylene (3) octylphenyl ether; or polyethylene glycol fatty acid esters, e.g. PEG-200 monolaurate, PEG-200 dilaurate, PEG-300 dilaurate, PEG-400 dilaurate, PEG-300 distearate, PEG-300 dioleate; alkylene glycol fatty acid mono esters, e.g. propylene glycol monolaurate (lauroglycol, such as lauroglycol FCC); or sucrose fatty acid esters, e.g. sucrose monostearate, sucrose distearate, sucrose monolaurate, sucrose dilaurate; or sorbitan fatty acid mono esters such as sorbitan mono laurate (Span 20), sorbitan monooleate, sorbitan monopalmitate (Span 40), or sorbitan stearate; or D-alpha-tocopheryl polyethylene glycol 1000 succinate; or a combination or mixture thereof; or block copolymers of ethylene oxide and propylene oxide, also known as polyoxyethylene polyoxypropylene block copolymers or polyoxyethylene polypropyleneglycol, such as Poloxamer 124, Poloxamer 188, Poloxamer 237, Poloxamer 388, or Poloxamer 407, or a combination of two or more thereof are employed for the preparation of the solid composition. More preferably, the present invention relates to the above-described process wherein, in addition to the sofosbuvir and the at least one matrix compound, less than 0.1 weight-%, preferably less than 0.01 weight-%, more preferably less than 0.001 weight-%, more preferably less than 0.0001 weight-%, more preferably in the range of from 0 to 0.00001 weight-% of a pharmaceutically acceptable surfactant having an HLB value of from 2-20 are employed for the preparation of the solid composition. More preferably, the present invention relates to the above-described process wherein, in addition to the sofosbuvir and the at least one matrix compound, less than 0.1 weight-%, preferably less than 0.01 weight-%, more preferably less than 0.001 weight-%, more preferably less than 0.0001 weight-%, more preferably in the range of from 0 to 0.00001 weight-% of a non-ionic surfactant are employed for the preparation of the solid composition. More preferably, the present invention relates to the above-described process wherein, in addition to the sofosbuvir and the at least one matrix compound, less than 0.1 weight-%, preferably less than 0.01 weight-%, more preferably less than 0.001 weight-%, more preferably less than 0.0001 weight-%, more preferably in the range of from 0 to 0.00001 weight-% of a surfactant are used for the preparation of the solid composition. In each case, the weight-% values are based on the total weight of the final solid composition obtained from the preparation process.

Preferably, the weight ratio of the solid sofosbuvir relative to the at least one matrix compound is in the range of from 5.5:4.5 to 9.5:0.5, more preferably in the range of from 5.5:4.5 to 9.2:0.8. More preferably, the weight ratio of the solid sofosbuvir relative to the at least one matrix compound is in the range of from 5.5:4.5 to 9:1, preferably in the range of from 6:4 to 8.5:1.5, more preferably in the range of from 7:3 to 8:2. Preferred ranges of the solid sofosbuvir relative to the at least one matrix compound are from 7:3 to 7.4:2.6 or from 7.2:2.8 to 7.6:2.4 or from 7.4:2.6 to 7.8:2.2 or from 7.6:2.4 to 8:2. A preferred range is also from 7.4:2.6 to 7.6:2.4. The term "the at least one matrix compound" as used in this context of the present invention relates to the sum of all matrix compounds employed.

Regarding the preferred matrix compounds, reference can be made to respective description above, in the section "The solid composition". In particular, it was found that preferred matrix compounds to be employed in the process of the present invention are characterized in that in the adsorption-desorption isotherms of these matrix compounds, the mass difference $\Delta m$(desorption) at 75% relative humidity and 25° C. is greater than or equal to the mass difference $\Delta m$(adsorption) at 75% relative humidity and 25° C. Even more preferably, the mass difference $\Delta m$(desorption) at 75% relative humidity and 25° C. is greater than the mass difference $\Delta m$(adsorption) at 75% relative humidity and 25° C.

Regarding the at least one pharmaceutically acceptable matrix compound, it was found that hydrophilic polymers, preferably hydrophilic water-soluble polymers, and silicon-based inorganic adsorbents are suitable matrix compounds. Preferably, the at least one matrix compound is selected from the group consisting of hydrophilic water-soluble polymers, silicon-based inorganic adsorbents and a combination of two or more thereof. For example, the at least one matrix compound is selected from the group consisting of hydrophilic polymers, preferably hydrophilic water-soluble polymers, and combinations of two or more thereof; or from the group consisting of silicon-based inorganic adsorbents and combinations of two or more thereof; or from the group consisting of combinations of at least one hydrophilic polymer, preferably hydrophilic water-soluble polymer, and at least one silicon-based inorganic adsorbent. Therefore, the present invention also relates to the above-described process, wherein the at least one matrix compound is selected from the group consisting of hydrophilic water-soluble polymers, silicon-based inorganic adsorbents and a combination of two or more thereof. Preferably, the silicon-based inorganic adsorbents have a pH in a defined range, preferably a pH of at least 6.0. More preferably, the silicon-based inorganic adsorbents have a pH in the range of from 6.0 to 9.0, more preferably in the range of from 6.5 to 8.5, more preferably in the range of from 7.0 to 8.0. Preferred pH ranges are, for example, from 7.0 to 7.4 or from 7.2 to 7.6 or from 7.4 to 7.8 or from 7.6 to 8.0.

According to the present invention, the sofosbuvir present in solution in at least one solvent is embedded in a matrix consisting of the at least one pharmaceutically acceptable matrix compound. Generally, all suitable processes can be used for embedding the solid sofosbuvir in the matrix consisting of the at least one pharmaceutically acceptable matrix compound.

Generally, no specific restrictions exist which solvent or which mixture or combination of solvents is used, provided that the sofosbuvir can be essentially dissolved therein at the chosen temperature and pressure conditions. The term "essentially dissolved" as used in this context of the present invention relates to a process wherein at least 99 weight-%, preferably at least 99.9 weight-%, more preferably at least 99.99 weight-% of the sofosbuvir is dissolved.

Preferably, the at least one solvent is selected from the group consisting of water, an organic solvent, and a combination of two or more thereof, such as a combination of water and at least one organic solvent or a combination of at least two organic solvents. Preferably, the organic solvent is selected from the group consisting of a C1-C2 halogenated hydrocarbon, a C1-C4 alcohol, such as a C1 alcohol, a C2 alcohol, a C3 alcohol, or a C4 alcohol; a C3-C6 ketone such as a C3 ketone, a C4 ketone, a C5 ketone, or a C6 ketone; a C2-C6 ether such as C2 ether, a C3 ether, a C4 ether, a C5 ether, or C6 ether; a C3-C5 ester such as a C3 ester, a C4 ester, or a C5 ester; and a combination of two or more thereof. A term "Cx" as used in this context of the present invention relates to the total number "x" of carbon atoms of the respective compound. For example, the term "C2 alcohol" includes ethanol or ethanediol, and the term "C3 ketone" includes acetone.

According to the process of the present invention, it is preferred that based on the sofosbuvir solution, a mixture is prepared which additionally contains the at least one matrix compound, wherein this mixture, depending on the chemical nature of the at least one solvent and the chemical nature of the at least one matrix compound, can be a solution or a dispersion, and that this mixture is subjected to at least one suitable drying process wherein, after the drying, at least 99 weight-%, preferably at least 99.9 weight-%, more preferably at least 99.9 weight % of the at least one solvent are removed and the solid composition is obtained.

Generally according to the process of the present invention, it is possible that the sofosbuvir is added with the at least one matrix compound to the at least one solvent and the resulting mixture is subjected to drying.

If two or more matrix compounds are employed, it is possible to add one or more first matrix compounds to the at least one solvent, to add the sofosbuvir to the resulting mixture, and to add one or more second matrix compounds to the resulting mixture comprising sofosbuvir. If two or more matrix compounds are employed, it is also possible to add the sofosbuvir to a first portion of the at least one solvent, to add the at least one matrix compound to a second portion of the at least one solvent, and to suitably combine the two resulting mixtures. If two or more matrix compounds are employed, it is also possible to add the sofosbuvir together with one or more first matrix compounds to a first portion of the at least one solvent, to add one or more second one matrix compound to a second portion of the at least one solvent, and to suitably combine the two resulting mixtures. Further, if two or more matrix compounds are employed, also other mixture sequences are conceivable.

If two or more solvents are employed, it is possible to add the sofosbuvir and the at least one matrix compound to one or more first solvents, and to add the resulting mixture to one or more second solvents. If two or more solvents are employed, it is also possible to add the sofosbuvir to one or more first solvents, to add the at least one matrix compound to one or more second solvents, and to suitably combine the two resulting mixtures. If two or more solvents are employed, it is also possible to add a first portion of the sofosbuvir and a first portion of the at least one matrix compound to one or more first solvents, to add a second portion of the sofosbuvir and a second portion of the at least one matrix compound to one or more second solvents, and to suitably combine the two resulting mixtures. Further, if two or more solvents are employed, also other mixing sequences are conceivable.

If two or more solvents and two or more matrix compounds are employed, the abovementioned mixture sequences can be suitably adapted accordingly.

According to a first preferred embodiment of the present invention, the at least one matrix compound is selected from the group consisting of silicon-based inorganic adsorbents and a combination of two or more thereof.

Regarding specific conceivable, preferred, and more preferred silicon-based inorganic adsorbents, reference is made to the respective disclosure in the section "The solid composition" hereinabove. Therefore, according to a preferred process of the present invention, the at least one silicon-based inorganic adsorbent is selected from the group consisting of silica, silicates, and a combination of two or more thereof, preferably having a pH in the range of from 6.0 to 9.0, more preferably in the range of from 6.5 to 8.5, more preferably in the range of from 7.0 to 8.0, wherein the silica is selected from the group consisting of fumed silica, precipitated silica, gel silica, colloidal silica, and a combination of two or more thereof, and wherein the silicates are aluminosilicates preferably comprising at least one alkali metal element and/or at least one alkaline earth metal element, more preferably at least one alkaline earth metal element, more preferably magnesium. According to a particularly preferred process of the present invention, the at least one silicon-based inorganic adsorbent, preferably having a pH in the range of from 6.0 to 9.0, more preferably in the range of from 6.5 to 8.5, more preferably in the range of from 7.0 to 8.0, is selected from the group consisting of silica and a combination of two or more thereof, wherein the silica is selected from the group consisting of fumed silica, precipitated silica, gel silica, colloidal silica, and a combination of two or more thereof. According to a further particularly preferred process of the present invention, the at least one silicon-based inorganic adsorbent, preferably having a pH in the range of from 6.0 to 9.0, more preferably in the range of from 6.5 to 8.5, more preferably in the range of from 7.0 to 8.0, is selected from the group consisting of silicates and a combination of two or more thereof, wherein the silicates are aluminosilicates preferably comprising at least one alkali metal element and/or at least one alkaline earth metal element, more preferably at least one alkaline earth metal element, more preferably magnesium.

In this case where the at least one matrix compound is selected from the group consisting of silicon-based inorganic adsorbents and a combination of two or more thereof, it is preferred that the process comprises melting the at least one matrix compound in solid form together with the sofosbuvir in solid form or that the process comprises dispersing the at least one matrix compound in the solution comprising the sofosbuvir.

Consequently, solvents are preferred in which the sofosbuvir can be dissolved and the at least one silicon-based inorganic adsorbent can be dispersed. Preferably, the at least one suitable solvent is selected from the group consisting of water, C1-C3 ketones, C1-C2 halogenated hydrocarbons, C3-C4 alcohols, C2-C6 ethers, C3-C5 esters, and a combination of two or more thereof, more preferably from the group consisting of C1-C3 ketones, and a combination of two or more thereof. More preferably, the at least one solvent comprises, more preferably consists of, acetone.

Regarding the weight ratio of the sofosbuvir and the at least one silicon-based inorganic adsorbent relative to the at least one solvent, no specific restrictions exist provided that the finally obtained mixture is a mixture wherein the at least one silicon-based inorganic adsorbent is dispersed in a solution of the sofosbuvir in the at least one solvent, which mixture can be subjected to a subsequent drying stage. Preferably, the weight ratio of the sofosbuvir plus the at least one silicon-based inorganic adsorbent, preferably the sofosbuvir plus the at least one silica, relative to the at least one solvent, preferably the acetone, is in the range of from 0.01:1 to 0.3:1, preferably in the range of from 0.02:1 to 0.2:1, more preferably in the range of from 0.05:1 to 0.2:1. Also preferably, the weight ratio of the sofosbuvir plus the at least one silicon-based inorganic adsorbent, preferably the sofosbuvir plus the at least one silicate, preferably the aluminosilicates preferably comprising at least one alkali metal element and/or at least one alkaline earth metal element, more preferably at least one alkaline earth metal element, more preferably magnesium, relative to the at least one solvent, preferably the acetone, is in the range of from 0.01:1 to 0.3:1, preferably in the range of from 0.02:1 to 0.2:1, more preferably in the range of from 0.05:1 to 0.2:1.

To accelerate and/or improve the solution process of the sofosbuvir in the at least one solvent, suitable methods can be applied. For example, the solution process can be influenced by choosing suitable temperatures, by stirring, and/or by subjecting the respective mixtures to sonication, wherein these methods can be applied during the entire or one or more parts of the mixing process.

Preferably, the dispersion of the at least one silicon-based inorganic adsorbent, preferably selected from the group consisting of silica, silicates, and a combination of two or more thereof, in the solution of the sofosbuvir in the at least one solvent, is prepared at a temperature in the range of from 10 to 40° C., more preferably in the range of from 15 to 35° C., more preferably in the range of from 20 to 30° C., preferably at ambient pressure.

As mentioned above, the dispersion comprising the sofosbuvir and the at least one matrix compound is preferably subjected to a drying stage. Therefore, the present invention also relates to the process as described above, wherein the embedding comprises subjecting the dispersion to drying.

Generally, no specific restrictions exist how said drying is carried. Conceivable drying methods include, but are not restricted to, direct drying, such as batch drying in a suitable oven or continuous drying or spray-drying or spray-granulation, for example in a band drying apparatus, or filtration or centrifugation followed by drying; indirect drying, such as drum drying or vacuum drying or evaporation; and freeze drying such as lyophilization. A combination of two or more different drying methods can be applied. Preferably, the dispersion of the at least one silicon-based inorganic adsorbent, preferably selected from the group consisting of silica, silicates, and a combination of two or more thereof, in the solution of the sofosbuvir in the at least one solvent, is subjected to drying comprising indirect drying, preferably comprising evaporation or filtration, more preferably comprising evaporation and vacuum drying, or comprising filtration and vacuum drying. Therefore, the present invention also relates to the process as described above, wherein the process comprises subjecting the dispersion of the at least one silicon-based inorganic adsorbent, preferably selected from the group consisting of silica, silicates, and a combination of two or more thereof, in the solution of the sofosbuvir in the at least one solvent, to drying by filtrating the dispersion or evaporating and optionally vacuum-drying the dispersion.

According to a second preferred embodiment of the present invention, the at least one matrix compound is selected from the group consisting of hydrophilic, preferably water-soluble, polymers and a combination of two or more thereof.

Regarding specific conceivable, preferred, and more preferred hydrophilic, preferably water-soluble, polymers, reference is made to the respective disclosure in the section "The solid composition" hereinabove. Therefore, according to a particularly preferred process of the present invention, the at least one hydrophilic, preferably water-soluble, polymer, comprises, preferably consists of a cellulose derivative selected from the group consisting of hydroxyalkylalkylcelluloses and a mixture of two or more thereof. More preferably, the at least one hydrophilic, preferably water-soluble, polymer, comprises, more preferably consists of, hydroxypropylmethylcellulose (HPMC) wherein the weight average molecular weight ($M_w$) of the cellulose derivative, preferably the hydroxyalkylalkylcellulose, more preferably the hydroxypropylmethylcellulose, is preferably in the range of from 7 to 225 kDa, more preferably in the range of from 7 to 100 kDa, more preferably in the range of from 7 to 30 kDa; and wherein the molecular degree of substitution (DS) of the cellulose derivative, preferably the hydroxyalkylalkylcellulose, more preferably the hydroxypropylmethylcellulose, is preferably in the range of from 0.3 to 2.8, more preferably in the range of from 0.6 to 2.5, more preferably in the range of from 1.0 to 2.3, more preferably in the range of from 1.3 to 2.0.

In this case where the at least one matrix compound is selected from the group consisting of hydrophilic water-soluble polymers and a combination of two or more thereof, it is preferred that the at least one matrix compound in solid form is melted together with the sofosbuvir in solid form or that a solution of the sofosbuvir and the at least one matrix compound is prepared.

Consequently, solvents are preferred in which the sofosbuvir as well as the at least one hydrophilic water-soluble polymer can be dissolved. Preferably, the at least one suitable solvent is selected from the group consisting of water, C1-C4 alcohol, C1-C2 halogenated hydrocarbon, a C3-C6 ketone, a C2-C6 ether, a C3-C5 ester, and a combination of two or more thereof, more preferably from the group consisting of water, C1-C4 alcohol, and a combination of two or more thereof. More preferably, the at least one solvent comprises water, more preferably water and at least one C1-C4 alcohol, more preferably water and one C1-C3 alcohol, more preferably water and one C1-C2 alcohol. More preferably, the at least one solvent comprises, more preferably consists of, water and ethanol.

Regarding the sequence of steps carried out for preparing the solution comprising the sofosbuvir and the at least one hydrophilic water-soluble polymer, no specific restrictions exist. For example, it is possible to add the sofosbuvir and the at least one hydrophilic water-soluble polymer to at least one solvent to obtain said mixture. It is also possible to add the sofosbuvir to the at least one solvent and add the at least one hydrophilic water-soluble polymer to the resulting mixture. It is also possible to add the at least one hydrophilic water-soluble polymer to the at least one solvent and add the sofosbuvir to the resulting mixture. If two or more solvents are employed, it is possible to add the sofosbuvir to one or more first solvents, to add the at least one hydrophilic water-soluble polymer to one or more second solvents, and to combine the resulting mixtures. If two or more solvents are employed, it is also possible to add the sofosbuvir and the at least one hydrophilic water-soluble polymer to one or more first solvents and add the resulting mixture to one or more second solvents. If two or more solvents are employed, it is also possible to add a first portion of the sofosbuvir and a first portion of the at least one hydrophilic water-soluble polymer to one or more first solvents, to add a second portion of the sofosbuvir and a second portion of the at least one hydrophilic water-soluble polymer to one or more second solvents, and to suitably combine the two resulting mixtures. Other mixing sequences are conceivable Preferably, the sofosbuvir and the at least one hydrophilic water-soluble polymer, preferably the sofosbuvir and the cellulose derivative selected from the group consisting of hydroxyalkylalkylcelluloses and a mixture of two or more thereof, more preferably the sofosbuvir and the hydroxypropylmethylcellulose, are added to one or more first solvents, preferably to one or more first solvents selected from the group consisting of water, C1-C4 alcohol, C1-C2 halogenated hydrocarbon, C3-C6 ketone, C2-C6 ether, C3-C5 ester, and a combination of two or more thereof, more preferably from the group consisting of water, C1-C4 alcohol, and a combination of two or more thereof, and the resulting mixture is added to one or more first second solvents, preferably to one or more first solvents selected from the group consisting of water, C1-C4 alcohol, C1-C2 halogenated hydrocarbon, C3-C6 ketone, C2-C6 ether, C3-C5 ester, and a combination of two or more thereof, more preferably from the group consisting of water, C1-C4 alcohol, and a combination of two or more thereof. More preferably, the sofosbuvir and the at least one hydrophilic water-soluble polymer, preferably the sofosbuvir and the cellulose derivative selected from the group consisting of hydroxyalkylalkylcelluloses and a mixture of two or more thereof, more preferably the sofosbuvir and the hydroxypropylmethylcellulose, are added to one or more C1-C4 alcohols, preferably to one or more C1-C2 alcohols, more preferably to one C1-C2 alcohol, more preferably to ethanol, and the resulting mixture is added to one or more solvents comprising water, preferably to water.

Regarding the weight ratio of the sofosbuvir and the at least one hydrophilic water-soluble polymer relative to the at least one solvent, no specific restrictions exist provided that the finally obtained mixture is a solution which can be subjected to a subsequent drying stage. Preferably, the weight ratio of the sofosbuvir and the at least one hydrophilic water-soluble polymer, preferably the sofosbuvir and the hydroxypropylmethylcellulose, relative to the at least one solvent, preferably the ethanol and the water, is in the range of from 0.01:1 to 0.3:1, preferably in the range of from 0.01:1 to 0.2:1, more preferably in the range of from 0.01:1 to 0.1:1.

To accelerate and/or improve the solution process of the sofosbuvir and the at least one hydrophilic water-soluble polymer in the at least one solvent, suitable methods can be applied. For example, the solution process can be influenced by choosing suitable temperatures, by stirring, and/or by subjecting the respective mixtures to sonication, wherein these methods can be applied during the entire or one or more parts of the mixing process.

Preferably, the solution of the sofosbuvir and the at least one hydrophilic water-soluble polymer, preferably the solution of the sofosbuvir and the cellulose derivative selected from the group consisting of hydroxyalkylalkylcelluloses and a mixture of two or more thereof, more preferably the solution of the sofosbuvir and the hydroxypropylmethylcellulose, is prepared at a temperature in the range of from 10 to 40° C., more preferably in the range of from 15 to 35° C., more preferably in the range of from 20 to 30° C., preferably at ambient pressure.

As mentioned above, the solution comprising the sofosbuvir and the at least one matrix compound is preferably subjected to a drying stage. Therefore, the present invention also relates to the process as described above, wherein the embedding comprises subjecting the solution to drying.

Generally, no specific restrictions exist how said drying is carried. Conceivable drying methods include, but are not restricted to, direct drying, such as batch drying in a suitable oven or continuous drying or spray-drying or spray-granulation, for example in a band drying apparatus, or filtration or centrifugation; indirect drying, such as drum drying or vacuum drying; and freeze drying such as lyophilization. A combination of two or more different drying methods can be applied. Preferably, the solution comprising the sofosbuvir and the at least one hydrophilic water-soluble polymer is subjected to direct drying, preferably spray-drying, or freeze drying, preferably lyophilization. Therefore, the present invention also relates to the process as described above, wherein the process comprises subjecting the solution comprising the sofosbuvir and the at least one hydrophilic water-soluble polymer to drying by lyophilizing the solution or spray-drying the solution.

From the process as described above, solid composition, preferably the solid compositions as described in the section "The solid composition" hereinabove, in particular the solid dispersion as described in the section "The solid composition" hereinabove, are obtainable or obtained. Therefore, the present invention also relates to a solid composition, preferably a solid composition comprising the sofosbuvir and the at least one hydrophilic water-soluble polymer, obtainable or obtained by a process as described above, in particular by a process comprising embedding sofosbuvir in a matrix consisting of the at least one hydrophilic water-soluble polymer, starting from a solution of the sofosbuvir in at least one solvent, wherein the weight ratio of the sofosbuvir relative to the at least one hydrophilic water-soluble polymer, is at least 5.5:4.5.

From the process as described above, solid composition, preferably the solid compositions as described in the section "The solid composition" hereinabove, in particular the solid dispersion as described in the section "The solid composition" hereinabove, are obtainable or obtained. Therefore, the present invention also relates to a solid composition, preferably a solid composition comprising the sofosbuvir and the at least one silicon-based inorganic adsorbent, preferably selected from the group consisting of silica, silicates, and a combination of two or more thereof, obtainable or obtained by a process as described above, in particular by a process comprising embedding sofosbuvir in a matrix consisting of at least one silicon-based inorganic adsorbent, preferably selected from the group consisting of silica, silicates, and a combination of two or more thereof, starting from a solution of the sofosbuvir in at least one solvent, wherein the weight ratio of the sofosbuvir relative to the at least one silicon-based inorganic adsorbent, preferably selected from the group consisting of silica, silicates, and a combination of two or more thereof, is at least 5.5:4.5.

The Pharmaceutical Composition

Yet further, the present invention also relates to a pharmaceutical composition comprising the solid composition described above. Preferably, the pharmaceutical composition is in the form of an oral dosage form which can be a compressed or a non-compressed dosage form. Preferably, the oral dosage form according to the present invention is a compressed dosage form. Preferably, the oral dosage form of the present invention is a granule, a capsule, for example a capsule filled with granules, a sachet, a pellet, a dragee, a lozenge, a troche, a pastille, or a tablet, such as an uncoated tablet, a coated tablet, an effervescent tablet, a soluble tablet, a dispersible tablet, an orodispersible tablet, a tablet for use in the mouth, a chewable tablet or an extrudate. More preferably, the oral dosage form of the present invention is a tablet.

Usually, the tablets contain, in addition to the solid composition of the present invention, at least one pharmaceutically acceptable excipient. Any pharmaceutically acceptable excipient can be employed as long as it does not detrimentally affect the properties of the pharmaceutical composition. Examples of generally conceivable pharmaceutically acceptable excipients comprise carriers such as solid carriers like magnesium carbonate, magnesium stearate, talc, sugar, lactose, pectin, dextrin, starch, gelatin, tragacanth, methylcellulose, sodium carboxymethylcellulose and wax; or liquid carriers such as water, aqueous or non-aqueous liquids, vehicles, diluents, solvents, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers, additives to make solutions isotonic, antifoaming agents, encapsulating material, surfactants, opacifing agents, enhancers, waxes, cap anti-locking agents (e.g. glycerol) and ion exchange resins. Other conceivable pharmaceutically acceptable additives are described in Remington's Pharmaceutical Sciences, 15$^{th}$ edition, Mack Publishing Co., New Jersey (1991). The terms "pharmaceutically acceptable excipient" and "pharmaceutical excipient" as used in this context of the present invention refer to a compound that is used to prepare a pharmaceutical composition, and is generally safe, non-toxic and neither biologically nor otherwise undesirable, and includes excipients that are acceptable for veterinary use as well as human pharmaceutical use.

According to a conceivable embodiment of the present invention, the pharmaceutical composition comprises the solid composition of the present invention, and at least one of compound selected from the group consisting of at least one of a diluent, at least one disintegrant, at least one glidant, at least one lubricant, and a combination of two or more thereof.

Conceivably, the diluent may be selected from the group consisting of calcium carbonate, dicalcium phosphate, dry starch, calcium sulfate, cellulose, compressible sugars, confectioner's sugar, dextrates, dextrin, dextrose, dibasic calcium phosphate dihydrate, glyceryl palmitostearate, hydrogenated vegetable oil, inositol, kaolin, lactose, magnesium carbonate, magnesium oxide, maltodextrin, mannitol, microcrystalline cellulose, polymethacrylates, potassium chloride, powdered cellulose, powdered sugar, pregelatinized starch, sodium chloride, sorbitol, starch, sucrose, sugar spheres, talc, tribasic calcium phosphate, and combinations of two or more thereof.

Conceivably, the disintegrant may be selected from the group consisting of agar, alginic acid, bentonite, carboxymethylcellulose calcium, carboxymethylcellulose sodium, carboxymethylcellulose, cellulose, a cation exchange resin, cellulose, gums, citrus pulp, colloidal silicon dioxide, corn starch, croscarmellose sodium crospovidone, guar gum, hydrous aluminum silicate, an ion exchange resin such as polyacrin potassium, magnesium aluminum silicate, methyl cellulose, microcrystalline cellulose, modified cellulose gum, modified corn starch, montmorillonite clay, natural sponge, polyacrilin potassium, potato starch, powdered cellulose, povidone, pregelatinized starch, sodium alginate, sodium bicarbonate in admixture with an acidulant such as tartaric acid or citric acid, sodium starch glycolate, starch, silicates such as, and combinations of two or more thereof.

Conceivably, the glidant may be selected from the group consisting of colloidal silicon dioxide, talc, starch, starch derivatives, and combinations of two or more thereof.

Conceivably, the lubricant may be selected from the group consisting of calcium stearate, glyceryl monostearate, glyceryl palmitostearate, hydrogenated castor oil, hydrogenated vegetable oil, light mineral oil, magnesium stearate, mineral oil, polyethylene glycol, sodium benzoate, sodium lauryl sulfate, sodium stearyl fumarate, stearic acid, talc, zinc stearate, and combinations thereof.

Conceivably, the pharmaceutical composition of the present invention, in particular in form of a tablet, may further comprise a coating agent which may further comprise a taste-masking agent. The coating agent may be formed from an aqueous film coat composition, wherein the aqueous film coat composition may comprise a film-forming polymer, water and/or an alcohol as a vehicle, and optionally one or more adjuvants such as are known in the film-coating art. The coating agent may be selected from among hydroxypropylmethylcellulose, hydroxypropylcellulose, methylcellulose, ethylcellulose, hydroxyethylcellulose, cellulose acetate phthalate, sodium ethyl cellulose sulfate, carboxymethyl cellulose, polyvinylpyrrolidone, zein, and an acrylic polymer such as methacrylic acid/methacrylic acid ester copolymers such as methacrylic acid/methylmethacrylate copolymers, etc., and a polyvinyl alcohol. With respect to the coating agent, film-forming polymers are typically provided in either aqueous or organic solvent-based solutions or aqueous dispersions. The polymers may be also provided in dry form, alone or in a powdery mixture with other components such as a plasticizer and/or a colorant, which may be made into a solution or dispersion. The aqueous film coat composition may further comprise water as a vehicle for the other components. The vehicle may optionally further comprise one or more water soluble solvents, such as an alcohol and/or a ketone. Conceivable examples of an alcohol include but are not limited to methanol, isopropanol, propanol, etc. A non-limiting example for the ketone may be acetone.

[0087] Suitable aqueous film coating compositions may include those commercially available from Colorcon, Inc. of West Point, Pa., under the trade name OPADRY and OPADRY II.

Therefore, the present invention also relates to the preparation of a pharmaceutical composition, preferably an oral dosage form, more preferably a tablet, wherein said pharmaceutical composition is preferably the pharmaceutical composition as described above, said process comprising
(a) providing a solid composition as described above, preferably by preparing a solid composition according to the processes as described above;
(b) admixing the solid composition provided according to (a), preferably prepared according to (a), with at least one pharmaceutically acceptable excipient.

Further, the present invention relates to the preparation of a pharmaceutical composition, preferably an oral dosage form, more preferably a tablet, wherein said pharmaceutical composition is preferably the pharmaceutical composition as described above, said process comprising
(a) providing a solid composition as described above, preferably by preparing a solid composition according to the processes as described above;
(b) admixing the solid composition provided according to (a), preferably prepared according to (a), with at least one pharmaceutically acceptable excipient;
(c) preferably compacting and forming the mixture obtained according to (b), obtaining an oral dosage form, preferably a tablet;
(d) optionally coating the tablet obtained according to (c) with at least one excipient.

Further, the present invention relates to a pharmaceutical composition, preferably an oral dosage form, more preferably a tablet, obtainable or obtained by a process for the preparation of a pharmaceutical composition, preferably an oral dosage form, more preferably a tablet, as described above.

Uses

The solid composition or the pharmaceutical composition, preferably the oral dosage form, more preferably the tablet of the present invention is preferably used in a method for treating hepatitis C in a human. Therefore, the present invention also relates to a solid composition or a pharmaceutical composition as described above, for use in a method for treating hepatitis C in a human. Further, the present invention relates to the use of a solid composition or a pharmaceutical composition as described above for treating hepatitis C in a human. Further, the present invention relates to the use of a solid composition or a pharmaceutical composition as described above for the preparation of a medicament for treating hepatitis C in a human. Further, the present invention relates to a method for treating hepatitis C comprising administering a solid composition or a pharmaceutical composition as described above to a human patient in need thereof.

Generally, the present invention also relates to the use of a pharmaceutically acceptable compound for stabilizing amorphous sofosbuvir according to formula (I)

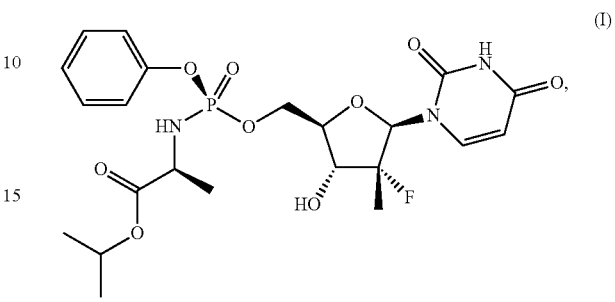

preferably in a solid composition, preferably in a solid dispersion, and/or in a pharmaceutical composition, wherein in the adsorption-desorption isotherm of the pharmaceutically acceptable compound, the mass difference $\Delta m$(desorption) at 75% relative humidity and 25° C. is greater than or equal to, preferably greater than, the mass difference $\Delta m$(adsorption) at 75% relative humidity and 25° C., determined according to dynamic vapor sorption measurement, wherein the pharmaceutically acceptable compound is preferably selected from the group consisting of hydrophilic water-soluble polymers, silicon-based inorganic adsorbents and a combination of two or more thereof.

Preferably, the present invention relates to the use as described above, wherein the pharmaceutically acceptable compound comprises, preferably consists of, a cellulose derivative selected from the group consisting of hydroxyalkylalkylcelluloses and a mixture of two or more thereof, the at least one hydrophilic water-soluble polymer preferably comprising, more preferably consisting of, hydroxypropylmethylcellulose (HPMC).

Also preferably, the present invention relates to the use as described above, wherein the pharmaceutically acceptable compound comprises, preferably consists of, a silicon-based inorganic adsorbent selected from the group consisting of silica, silicates, and a combination of two or more thereof, wherein the silica is preferably selected from the group consisting of fumed silica, precipitated silica, gel silica, colloidal silica, and a combination of two or more thereof, and wherein the silicates are preferably aluminosilicates preferably comprising at least one alkali metal element and/or at least one alkaline earth metal element, more preferably at least one alkaline earth metal element, more preferably magnesium, wherein more preferably, at least 90 weight-%, more preferably at least 95 weight-%, more preferably at least 99 weight-% of the at least one silicon-based inorganic adsorbent are present in amorphous form, and wherein, more preferably, the pharmaceutically acceptable compound has a pH in the range of from 6.0 to 9.0, preferably in the range of from 6.5 to 8.5, more preferably in the range of from 7.0 to 8.0.

Also preferably, the present invention relates to the use of a pharmaceutically acceptable compound for stabilizing amorphous sofosbuvir according to formula (I)

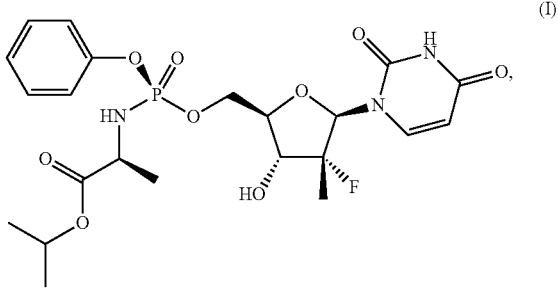 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

in a solid composition, preferably in a solid dispersion, and/or in a pharmaceutical composition, wherein the solid composition contains the amorphous sofosbuvir in an amount of at least 55 weight-%, preferably of from 55 to 90 weight-%, more preferably of from 60 to 85 weight-%, more preferably of from 70 to 80 weight-%, based on the combined weight of the amorphous sofosbuvir and the pharmaceutically acceptable compound, wherein the pharmaceutically acceptable compound is preferably selected from the group consisting of hydrophilic water-soluble polymers, silicon-based inorganic adsorbents and a combination of two or more thereof, and wherein in the adsorption-desorption isotherm of the pharmaceutically acceptable compound, the mass difference Δm(desorption) at 75% relative humidity and 25° C. is preferably greater than or equal to, preferably greater than, the mass difference Δm(adsorption) at 75% relative humidity and 25° C., determined according to dynamic vapor sorption measurement. Preferred ranges of the sofosbuvir content of the solid composition are from 70 to 74 weight-% or from 72 to 76 weight-% or from 74 to 78 weight-% or from 76 to 80 weight-%, based on the combined weight of the sofosbuvir and the pharmaceutically acceptable compound. A preferred range is also from 74 to 76 weight-%.

Also preferably, the present invention relates to the use of a pharmaceutically acceptable compound for stabilizing amorphous sofosbuvir according to formula (I)

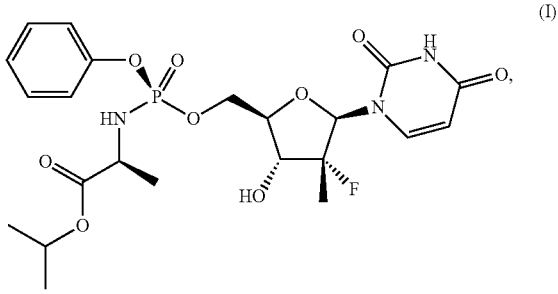 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

in a solid composition, preferably in a solid dispersion, and/or in a pharmaceutical composition, wherein in the adsorption-desorption isotherm of the pharmaceutically acceptable compound, the mass difference Δm(desorption) at 75% relative humidity and 25° C. is greater than or equal to, preferably greater than, the mass difference Δm(adsorption) at 75% relative humidity and 25° C., determined according to dynamic vapor sorption measurement, wherein the pharmaceutically acceptable compound is preferably selected from the group consisting of hydrophilic water-soluble polymers, silicon-based inorganic adsorbents and a combination of two or more thereof, wherein the solid composition contains the amorphous sofosbuvir preferably in an amount of at least 55 weight-%, more preferably of from 55 to 90 weight-%, more preferably of from 60 to 85 weight-%, more preferably of from 70 to 80 weight-%, based on the combined weight of the amorphous sofosbuvir and the pharmaceutically acceptable compound. Preferred ranges of the sofosbuvir content of the solid composition are from 70 to 74 weight-% or from 72 to 76 weight-% or from 74 to 78 weight-% or from 76 to 80 weight-%, based on the combined weight of the sofosbuvir and the pharmaceutically acceptable compound. A preferred range is also from 74 to 76 weight-%.

Also preferably, the present invention relates to the use of a pharmaceutically acceptable compound for stabilizing amorphous sofosbuvir according to formula (I)

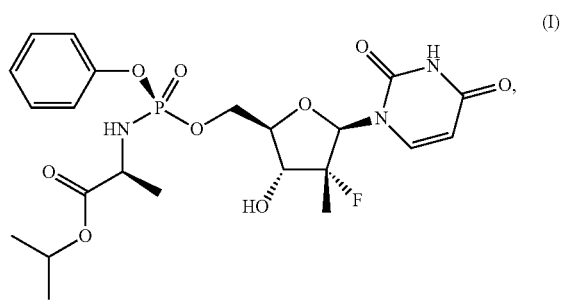 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

in a solid composition, preferably in a solid dispersion, and/or in a pharmaceutical composition, wherein in the adsorption-desorption isotherm of the pharmaceutically acceptable compound, the mass difference Δm(desorption) at 75% relative humidity and 25° C. is greater than or equal to, preferably greater than, the mass difference Δm(adsorption) at 75% relative humidity and 25° C., determined according to dynamic vapor sorption measurement, wherein the pharmaceutically acceptable compound is preferably selected from the group consisting of hydrophilic water-soluble polymers, silicon-based inorganic adsorbents and a combination of two or more thereof, wherein the solid composition contains the amorphous sofosbuvir in an amount of at least 55 weight-%, preferably of from 55 to 90 weight-%, more preferably of from 60 to 85 weight-%, more preferably of from 70 to 80 weight-%, based on the combined weight of the amorphous sofosbuvir and the pharmaceutically acceptable compound. Preferred ranges of the sofosbuvir content of the solid composition are from 70 to 74 weight-% or from 72 to 76 weight-% or from 74 to 78 weight-% or from 76 to 80 weight-%, based on the combined weight of the sofosbuvir and the pharmaceutically acceptable compound. A preferred range is also from 74 to 76 weight-%.

Preferably, the present invention relates to the use of hydroxypropylmethylcellulose for stabilizing solid amorphous sofosbuvir according to formula (I)

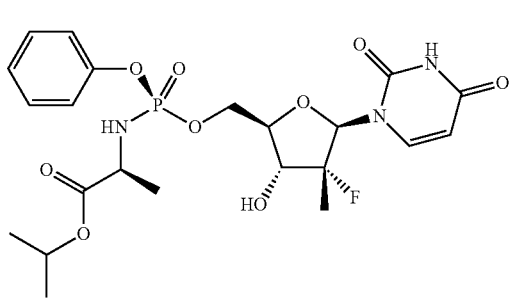

(I)

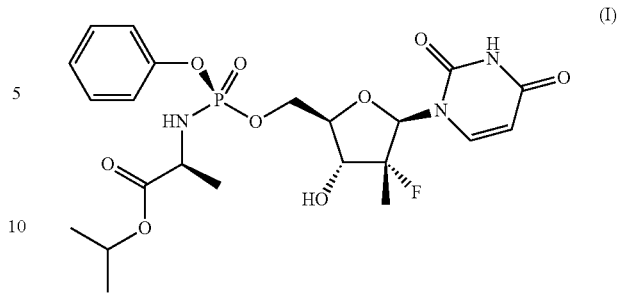

(I)

in a solid composition, preferably a solid dispersion, containing the hydroxypropylmethylcellulose and the sofosbuvir in an amount of at least 55 weight-%, preferably in an amount in the range of from 55 to 90 weight-%, more preferably from 60 to 85 weight-%, more preferably from 70 to 80 weight-%, based on the combined weight of the sofosbuvir and the hydroxypropylmethylcellulose, wherein preferably at least 99.5 weight-%, more preferably at least 99.9 weight-% of the solid composition consist of the sofosbuvir and the hydroxypropylmethylcellulose, wherein the solid composition preferably contains less than 0.1 weight-%, more preferably less than 0.01 weight-%, more preferably less than 0.001 weight-% of a surfactant.

Also preferably, the present invention relates to the use of hydroxypropylmethylcellulose for stabilizing solid amorphous sofosbuvir according to formula (I)

in a solid composition, preferably a solid dispersion, containing the hydroxypropylmethylcellulose and the sofosbuvir in an amount of at least 55 weight-%, preferably in an amount in the range of from 55 to 90 weight-%, more preferably from 60 to 85 weight-%, more preferably from 70 to 80 weight-%, based on the combined weight of the sofosbuvir and the hydroxypropylmethylcellulose, wherein in the adsorption-desorption isotherm of the hydroxypropylmethylcellulose, the mass difference $\Delta m(desorption)$ at 75% relative humidity and 25° C. is greater than or equal to, preferably greater than, the mass difference $\Delta m(adsorption)$ at 75% relative humidity and 25° C., determined according to dynamic vapor sorption measurement, wherein preferably at least 99.5 weight-%, more preferably at least 99.9 weight-% of the solid composition consist of the sofosbuvir and the hydroxypropylmethylcellulose, wherein the solid composition preferably contains less than 0.1 weight-%, more preferably less than 0.01 weight-%, more preferably less than 0.001 weight-% of a surfactant, In particular, the present invention generally relates to the use of hydroxypropylmethylcellulose for stabilizing solid amorphous sofosbuvir according to formula (I)

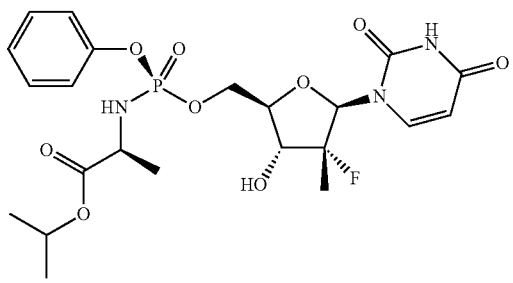

(I)

(I)

in a solid composition, preferably a solid dispersion, wherein in the adsorption-desorption isotherm of the hydroxypropylmethylcellulose, the mass difference $\Delta m(desorption)$ at 75% relative humidity and 25° C. is greater than or equal to, preferably greater than, the mass difference $\Delta m(adsorption)$ at 75% relative humidity and 25° C., determined according to dynamic vapor sorption measurement, wherein preferably at least 99.5 weight-%, more preferably at least 99.9 weight-% of the solid composition consist of the sofosbuvir and the hydroxypropylmethylcellulose, wherein the solid composition preferably contains less than 0.1 weight-%, more preferably less than 0.01 weight-%, more preferably less than 0.001 weight-% of a surfactant.

Also preferably, the present invention relates to the use of hydroxypropylmethylcellulose for stabilizing solid amorphous sofosbuvir according to formula (I)

in a solid composition, preferably a solid dispersion, containing the hydroxypropylmethylcellulose and the sofosbuvir in an amount of at least 55 weight-%, preferably in an amount in the range of from 55 to 90 weight-%, more preferably from 60 to 85 weight-%, more preferably from 70 to 80 weight-%, based on the combined weight of the sofosbuvir and the hydroxypropylmethylcellulose, wherein preferably at least 99.5 weight-%, more preferably at least 99.9 weight-% of the solid composition consist of the sofosbuvir and the hydroxypropylmethylcellulose, wherein the solid composition preferably contains less than 0.1 weight-%, more preferably less than 0.01 weight-%, more preferably less than 0.001 weight-% of a surfactant, more preferably, in the adsorption-desorption isotherm of the hydroxypropylmethylcellulose, the mass difference $\Delta m(desorption)$ at 75% relative humidity and 25° C. is greater than or equal to, preferably greater than, the mass difference Δm(adsorption) at 75% relative humidity and 25° C., determined according to dynamic vapor sorption measurement.

The present invention is illustrated by the following embodiments and combinations of embodiments resulting from the given dependencies and back-references:

1. A solid composition comprising sofosbuvir according to formula (I)

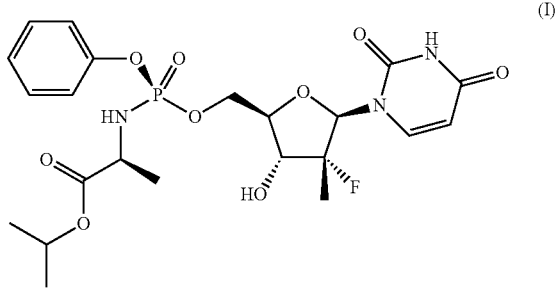 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

and at least one pharmaceutically acceptable matrix compound wherein at least 99 weight-% of the sofosbuvir comprised in the composition are present in amorphous form, at least 99 weight-% of the solid composition consist of the sofosbuvir and the at least one matrix compound, and wherein the solid composition contains the sofosbuvir in an amount of at least 55 weight-% based on the combined weight of the sofosbuvir and the at least one matrix compound.

2. The solid composition of embodiment 1, containing the sofosbuvir in an amount in the range of from 55 to 90 weight-%, preferably from 60 to 85 weight-%, more preferably from 70 to 80 weight-%, based on the combined weight of the sofosbuvir and the at least one matrix compound.

3. The solid composition of embodiment 1 or 2, wherein in the adsorption-desorption isotherm of the at least one pharmaceutically acceptable matrix compound, the mass difference Δm(desorption) at 75% relative humidity and 25° C. is greater than or equal to, preferably greater than, the mass difference Δm(adsorption) at 75% relative humidity and 25° C., determined according to dynamic vapor sorption measurement.

4. The solid composition of any of embodiments 1 to 3, wherein the at least one matrix compound is selected from the group consisting of hydrophilic water-soluble polymers, silicon-based inorganic adsorbents and a combination of two or more thereof.

5. The solid composition of any of embodiments 1 to 4, wherein the at least one matrix compound comprises at least one silicon-based inorganic adsorbent, preferably consists of at least one silicon-based inorganic adsorbent.

6. The solid composition of embodiment 5, wherein the at least one silicon-based inorganic adsorbent has an oil adsorbance in the range of from 1.0 to 5.0 ml/g, preferably in the range of from 1.5 to 4.0 ml/g.

7. The solid composition of embodiment 5 or 6, wherein the at least one silicon-based inorganic adsorbent has a bulk density in the range of from 10 to 500 g/ml, preferably in the range of from 30 to 400 g/ml, more preferably in the range of from 50 to 300 g/ml.

8. The solid composition of any of embodiments 5 to 7, wherein the at least one silicon-based inorganic adsorbent is selected from the group consisting of silica, silicates, and a combination of two or more thereof, wherein the silica is preferably selected from the group consisting of fumed silica, precipitated silica, gel silica, colloidal silica, and a combination of two or more thereof, and wherein the silicates are preferably aluminosilicates preferably comprising at least one alkali metal element and/or at least one alkaline earth metal element, more preferably at least one alkaline earth metal element, more preferably magnesium, wherein more preferably, at least 90 weight-%, more preferably at least 95 weight-%, more preferably at least 99 weight-% of the at least one silicon-based inorganic adsorbent are present in amorphous form.

9. The solid composition of any of embodiments 5 to 8, wherein the at least one matrix compound has a pH in the range of from 6.0 to 9.0, preferably in the range of from 6.5 to 8.5, more preferably in the range of from 7.0 to 8.0.

10. The solid composition of any of embodiments 1 to 4, wherein the at least one matrix compound comprises at least one hydrophilic water-soluble polymer, preferably consists of at least one hydrophilic water-soluble polymer.

11. The solid composition of embodiment 10, wherein the at least one hydrophilic water-soluble polymer has a solubility in water of at least 10 g/l, preferably of at least 20 g/l, more preferably of at least 30 g/l, in each case at 23° C. at atmospheric pressure.

12. The solid composition of embodiment 10 or 11, wherein the at least one hydrophilic water-soluble polymer comprises, preferably consists of a cellulose derivative selected from the group consisting of hydroxyalkylalkylcelluloses and a mixture of two or more thereof, the at least one hydrophilic water-soluble polymer preferably comprising, more preferably consisting of, hydroxypropylmethylcellulose (HPMC).

13. The solid composition of embodiment 12, wherein the cellulose derivative has a degree of substitution (DS) in the range of from 0.3 to 2.8, preferably in the range of from 0.6 to 2.5, more preferably in the range of from 1.0 to 2.3, more preferably in the range of from 1.3 to 2.0.

14. The solid composition of embodiment 12 or 13, wherein the weight average molecular weight ($M_w$) of the cellulose derivative is in the range of from 7 to 225 kDa, preferably in the range of from 7 to 100 kDa, more preferably in the range of from 7 to 30 kDa.

15. The solid composition of any of embodiments 1 to 14, wherein at least 99.5 weight-%, preferably at least 99.9 weight-% of the sofosbuvir comprised in the composition are present in amorphous form.

16. The solid composition of any of embodiments 1 to 15, wherein at least 99.5 weight-%, preferably at least 99.9 weight-% of the solid composition consist of the sofosbuvir and the at least one matrix compound.

17. The solid composition of any of embodiments 1 to 16, comprising less than 0.1 weight %, preferably less than 0.01 weight-%, more preferably less than 0.001 weight-% of a surfactant.

18. The solid composition of any of embodiments 1 to 17, having a moisture stability of at least 95%, preferably at least 98%, more preferably at least 99%, wherein the moisture stability is defined as the amount of solid amorphous sofosbuvir which is present in the solid composition after having been exposed to a relative humidity of 75% at 40° C. for 8 weeks, relative to the amount of solid amorphous sofosbuvir which is present in the solid composition before said exposure.

19. The solid composition of any of embodiments 1 to 18, being a solid dispersion.

20. A pharmaceutical composition comprising the solid composition according to any of embodiments 1 to 19.
21. The pharmaceutical composition of embodiment 20, being an oral dosage form, preferably a tablet.
22. A process for the preparation of a solid composition, comprising sofosbuvir according to formula (I)

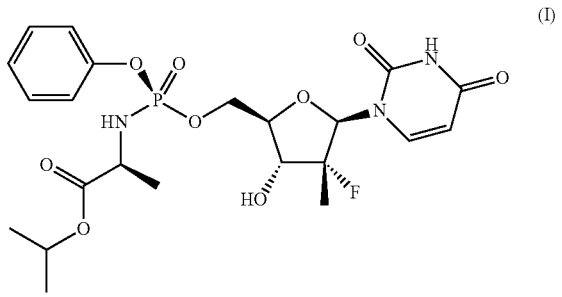 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

(I)

and at least one pharmaceutically acceptable matrix compound, preferably for the preparation of a solid composition according to any of embodiments 1 to 19, said process comprising embedding sofosbuvir in a matrix consisting of the at least one pharmaceutically acceptable matrix compound, starting from a solution of the sofosbuvir in at least one solvent, wherein the weight ratio of the sofosbuvir relative to the at least one matrix compound is at least 5.5:4.5, preferably in the range of from 5.5:4.5 to 9:1, more preferably in the range of from 6:4 to 8.5:1.5, more preferably in the range of from 7: 3 to 8:2.23. A process for the preparation of a solid composition, comprising sofosbuvir according to formula (I)

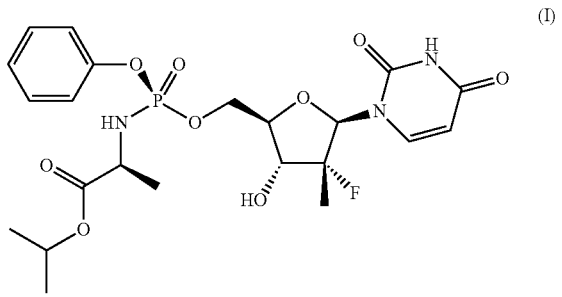 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

(I)

and at least one pharmaceutically acceptable matrix compound, preferably for the preparation of a solid composition according to any of embodiments 1 to 19, said process comprising embedding sofosbuvir in a matrix consisting of the at least one pharmaceutically acceptable matrix compound by melting the at least one pharmaceutically acceptable matrix compound in solid form together with the sofosbuvir in solid form, preferably by a hot-melt method, more preferably by a hot-melt extrusion method, wherein the weight ratio of the sofosbuvir relative to the at least one matrix compound is at least 5.5:4.5, preferably in the range of from 5.5:4.5 to 9:1, more preferably in the range of from 6:4 to 8.5:1.5, more preferably in the range of from 7:3 to 8:2.
24. The process of embodiment 22 or 23, wherein in the adsorption-desorption isotherm of the at least one matrix compound, the mass difference Δm(desorption) at 75% relative humidity and 25° C. is greater than or equal to, preferably greater than, the mass difference Δm(adsorption) at 75% relative humidity and 25° C., determined according to dynamic vapor sorption measurement.
25. The process of any of embodiments 22 to 24, wherein the at least one matrix compound is selected from the group consisting of hydrophilic water-soluble polymers, silicon-based inorganic adsorbents and a combination of two or more thereof
26. The process of any of embodiments 22 or 24 or 25, wherein the at least one solvent is selected from the group consisting of water, an organic solvent, and a combination of two or more thereof, wherein the organic solvent is preferably selected from the group consisting of a C1-C2 halogenated hydrocarbon, a C1-C4 alcohol, a C3-C6 ketone, a C2-C6 ether, a C3-C5 ester, and a combination of two or more thereof.
27. The process of any of embodiments 22 or 24 to 26, wherein the at least one matrix compound is selected from the group consisting of hydrophilic water-soluble polymers and a combination of two or more thereof and wherein the embedding comprises preparing a solution of the sofosbuvir and the at least one matrix compound in at least one solvent.
28. The process of embodiment 27, wherein the at least one solvent is selected from the group consisting of water, C1-C4 alcohols, C1-C2 halogenated hydrocarbons, C3-C6 ketones, C2-C6 ethers, C3-C5 esters, and a combination of two or more thereof.
29. The process of embodiment 27 or 28, wherein the embedding comprises subjecting the solution to drying, preferably by lyophilizing the solution or spray-drying the solution.
30. The process of any of embodiments 22 or 24 to 26, wherein the at least one matrix compound is selected from the group consisting of silicon-based inorganic adsorbents and a combination of two or more thereof and wherein the embedding comprises dispersing the at least one matrix compound in the solution.
31. The process of embodiment 30, wherein the at least one matrix compound has a pH in the range of from 6.0 to 9.0, preferably in the range of from 6.5 to 8.5, more preferably in the range of from 7.0 to 8.0.
32. The process of embodiment 30 or 31, wherein the at least one solvent is selected from the group consisting of water, C1-C3 ketones, C1-C2 halogenated hydrocarbons, C3-C4 alcohols, C2-C6 ethers, C3-C5 esters, and a combination of two or more thereof
33. The process of any of embodiments 30 to 32, wherein the embedding comprises subjecting the dispersion to drying, preferably filtrating the dispersion or evaporating the dispersion, preferably followed by vacuum drying.
34. The process of any of embodiments 22 or 24 to 33, wherein the solution of the sofosbuvir in at least one solvent is prepared from sofosbuvir of which at least 95 weight-%, preferably at least 99 weight-%, more preferably at least 99.9 weight-% are present in its amorphous form.
35. The process of embodiment 34, wherein the sofosbuvir is prepared by a method comprising
(i) providing sofosbuvir in at least one crystalline form or in amorphous form or as a mixture of at least one crystalline form and amorphous form, preferably providing sofosbuvir of which at least 95 weight-%, preferably at least 99 weight-%, more preferably at least 99.9 weight-% are present in at least one crystalline form;
(ii) dissolving at least a portion of the sofosbuvir provided according to (i) in at least one solvent, obtaining a solution comprising the sofosbuvir;
(iii) subjecting at least a portion of the solution obtained according to (ii), optionally after concentrating, to lyophilization or rapid-drying, preferably rapid-drying, obtaining the sofosbuvir of which at least 95 weight-%, preferably at least 99 weight-%, more preferably at least 99.9 weight-% are present in its amorphous form.

36. The process of embodiment 35, wherein the at least one solvent according to (ii) is selected from the group consisting of water, C1-C3 ketones, C1-C2 halogenated hydrocarbons, C1-C4 alcohols, C2-C6 ethers, C3-C5 esters, and a combination of two or more thereof, more preferably from the group consisting of water, C1-C4 alcohols, C1-C3 ketones, and a combination of two or more thereof, wherein more preferably, the at least one solvent comprises, more preferably consists of, water and a C1-C4 alcohol, preferably water and ethanol, or comprises, more preferably consists of, acetone.

37. The process of embodiment 35 or 36, wherein the rapid-drying is carried out by spray-drying or spray-granulation, preferably by spray-drying, wherein the spray-drying is preferably carried out at an inlet temperature in the range of from 50 to 100° C., and at an outlet temperature in the range of from 20 to 70° C.

38. The process of embodiment 34, wherein the sofosbuvir is prepared by a method comprising
(i) providing sofosbuvir in at least one crystalline form or in amorphous form or as a mixture of at least one crystalline form and amorphous form, preferably providing sofosbuvir of which at least 95 weight-%, preferably at least 99 weight-%, more preferably at least 99.9 weight-% are present in at least one crystalline form;
(ii) subjecting the sofosbuvir provided in (i) to a melt method, preferably a hot-melt method, more preferably a hot-melt extrusion method, obtaining the sofosbuvir of which at least 95 weight-%, preferably at least 99 weight-%, more preferably at least 99.9 weight-% are present in its amorphous form.

39. A process for the preparation of a pharmaceutical composition, preferably an oral dosage form, more preferably a tablet, said process comprising
(a) providing a solid composition according to any of embodiments 1 to 19, preferably by preparing a solid composition according to a process according to any of embodiments 22 to 38;
(b) admixing the solid composition provided according to (a), preferably preparable or prepared according to (a), with at least one pharmaceutically acceptable excipient.

40. A solid composition, obtainable or obtained by a process according to any of embodiments 22 to 38.

41. A pharmaceutical composition, obtainable or obtained by a process according to embodiment 39.

42. A solid composition according to any of embodiments 1 to 19 or 40, or a pharmaceutical composition according to any of embodiments 20, 21 or 41, for use in a method for treating hepatitis C in a human.

43. Use of a solid composition according to any of embodiments 1 to 19 or 40, or a pharmaceutical composition according to any of embodiments 20, 21 or 41, for treating hepatitis C in a human.

44. Use of a solid composition according to any of embodiments 1 to 19 or 40, or a pharmaceutical composition according to any of embodiments 20, 21 or 41, for the preparation of a medicament for treating hepatitis C in a human.

45. A method for treating hepatitis C comprising administering a solid composition according to any of embodiments 1 to 19 or 40, or a pharmaceutical composition according to any of embodiments 20, 21 or 41, to a human patient in need thereof.

46. Use of a pharmaceutically acceptable compound for stabilizing amorphous sofosbuvir according to formula (I)

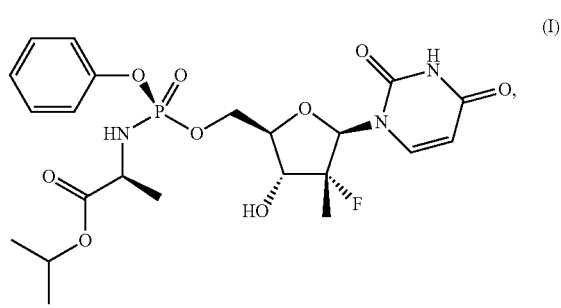 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

preferably in a solid composition, preferably in a solid dispersion, and/or in a pharmaceutical composition, wherein in the adsorption-desorption isotherm of the pharmaceutically acceptable compound, the mass difference Δm(desorption) at 75% relative humidity and 25° C. is greater than or equal to, preferably greater than, the mass difference Δm(adsorption) at 75% relative humidity and 25° C., determined according to dynamic vapor sorption measurement.

47. The use of embodiment 46, wherein the solid composition contains amorphous sofosbuvir in an amount of at least 55 weight-%, preferably of from 55 to 90 weight-%, more preferably of from 60 to 85 weight-%, more preferably of from 70 to 80 weight-%, based on the combined weight of the amorphous sofosbuvir and the pharmaceutically acceptable compound, wherein preferably at least 99 weight-%, more preferably at least 99.5 weight-%, more preferably at least 99.9 weight-% of the solid composition consist of the sofosbuvir and the pharmaceutically acceptable compound.

48. Use of a pharmaceutically acceptable compound for stabilizing amorphous sofosbuvir according to formula (I)

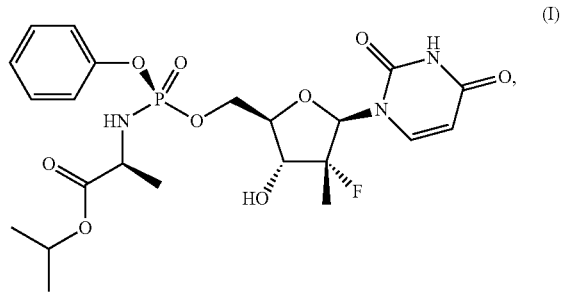 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

in a solid composition, preferably in a solid dispersion, and/or in a pharmaceutical composition, wherein the solid composition contains the amorphous sofosbuvir in an amount of at least 55 weight-%, preferably of from 55 to 90 weight-%, more preferably of from 60 to 85 weight-%, more preferably of from 70 to 80 weight-%, based on the combined weight of the amorphous sofosbuvir and the pharmaceutically acceptable compound, wherein preferably at least 99 weight-%, more preferably at least 99.5 weight-%, more preferably at least 99.9 weight-% of the solid composition consist of the sofosbuvir and the pharmaceutically acceptable compound.

49. The use of embodiment 48, wherein in the adsorption-desorption isotherm of the pharmaceutically acceptable compound, the mass difference Δm(desorption) at 75% relative humidity and 25° C. is preferably greater than or equal to, preferably greater than, the mass difference Δm(adsorption) at 75% relative humidity and 25° C., determined according to dynamic vapor sorption measurement.

50. The use of any of embodiments 46 to 49, wherein the pharmaceutically acceptable compound is selected from the group consisting of hydrophilic water-soluble polymers, silicon-based inorganic adsorbents and a combination of two or more thereof 51. The use of any of embodiments 46 to 50, wherein the pharmaceutically acceptable compound comprises, preferably consists of, a cellulose derivative selected from the group consisting of hydroxyalkylalkylcelluloses and a mixture of two or more thereof, the at least one hydrophilic water-soluble polymer preferably comprising, more preferably consisting of, hydroxypropylmethylcellulose (HPMC).

52. The use of any of embodiments 46 to 50, wherein the pharmaceutically acceptable compound comprises, preferably consists of, a silicon-based inorganic adsorbent selected from the group consisting of silica, silicates, and a combination of two or more thereof, wherein the silica is preferably selected from the group consisting of fumed silica, precipitated silica, gel silica, colloidal silica, and a combination of two or more thereof, and wherein the silicates are preferably aluminosilicates preferably comprising at least one alkali metal element and/or at least one alkaline earth metal element, more preferably at least one alkaline earth metal element, more preferably magnesium, wherein more preferably, at least 90 weight-%, more preferably at least 95 weight-%, more preferably at least 99 weight-% of the at least one silicon-based inorganic adsorbent are present in amorphous form.

53. The use of embodiment 52, wherein the pharmaceutically acceptable compound has a pH in the range of from 6.0 to 9.0, preferably in the range of from 6.5 to 8.5, more preferably in the range of from 7.0 to 8.0.

54. Use of hydroxypropylmethylcellulose for stabilizing amorphous sofosbuvir according to formula (I)

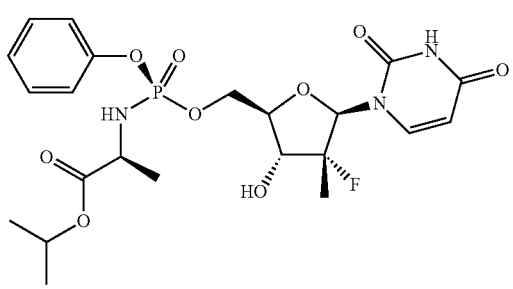

(I)

in a solid composition containing the sofosbuvir in an amount of at least 55 weight-%, preferably in an amount in the range of from 55 to 90 weight-%, more preferably from 60 to 85 weight-%, more preferably from 70 to 80 weight-%, based on the combined weight of the sofosbuvir and the hydroxypropylmethylcellulose, wherein preferably at least 99 weight-%, more preferably at least 99.5 weight-%, more preferably at least 99.9 weight-% of the solid composition consist of the sofosbuvir and the hydroxypropylmethylcellulose.

55. Use of hydroxypropylmethylcellulose for stabilizing amorphous sofosbuvir according to formula (I)

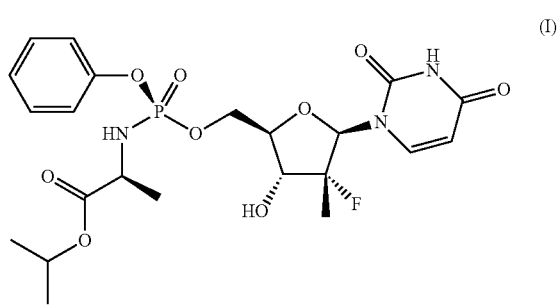 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

(I)

in a solid composition, wherein in the adsorption-desorption isotherm of the hydroxypropylmethylcellulose, the mass difference Δm(desorption) at 75% relative humidity and 25° C. is greater than or equal to, preferably greater than, the mass difference Δm(adsorption) at 75% relative humidity and 25° C., determined according to dynamic vapor sorption measurement, wherein preferably at least 99 weight-%, more preferably at least 99.5 weight-%, more preferably at least 99.9 weight-% of the solid composition consist of the sofosbuvir and the hydroxypropylmethylcellulose.

56. Use of hydroxypropylmethylcellulose for stabilizing amorphous sofosbuvir according to formula (I)

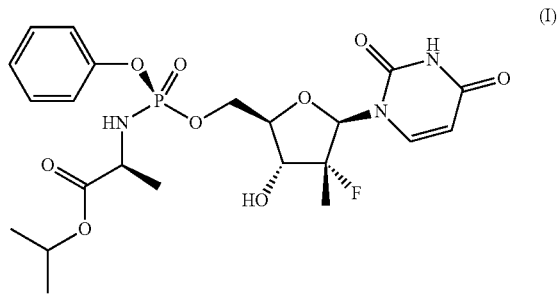 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

(I)

in a solid composition containing the sofosbuvir in an amount of at least 55 weight-%, preferably in an amount in the range of from 55 to 90 weight-%, more preferably from 60 to 85 weight-%, more preferably from 70 to 80 weight-%, based on the combined weight of the sofosbuvir and the hydroxypropylmethylcellulose, wherein in the adsorption-desorption isotherm of the hydroxypropylmethylcellulose, the mass difference Δm(desorption) at 75% relative humidity and 25° C. is greater than or equal to, preferably greater than, the mass difference Δm(adsorption) at 75% relative humidity and 25° C., determined according to dynamic vapor sorption measurement wherein preferably at least 99 weight-%, more preferably at least 99.5 weight-%, more preferably at least 99.9 weight-% of the solid composition consist of the sofosbuvir and the hydroxypropylmethylcellulose.
57. The use of any of embodiments 54 to 56, wherein the solid composition preferably contains less than 0.1 weight-%, more preferably less than 0.01 weight-%, more preferably less than 0.001 weight-% of a surfactant.
58. A process for the preparation of sofosbuvir of which at least 95 weight-%, preferably at least 99 weight-%, more preferably at least 99.9 weight-% are present in its amorphous form, comprising
   (i) providing sofosbuvir in at least one crystalline form or in amorphous form or as a mixture of at least one crystalline form and amorphous form, preferably providing sofosbuvir of which at least 95 weight-%, preferably at least 99 weight-%, more preferably at least 99.9 weight-% are present in at least one crystalline form;
   (ii) dissolving at least a portion of the sofosbuvir provided according to (i) in at least one solvent, obtaining a solution comprising the sofosbuvir;
   (iii) subjecting at least a portion of the solution obtained according to (ii), optionally after concentrating, to rapid-drying, obtaining the sofosbuvir of which at least 95 weight-%, preferably at least 99 weight-%, more preferably at least 99.9 weight-% are present in its amorphous form.
59. The process of embodiment 58, wherein the at least one solvent according to (ii) is selected from the group consisting of water, C1-C3 ketones, C1-C2 halogenated hydrocarbons, C1-C4 alcohols, C2-C6 ethers, C3-C5 esters, and a combination of two or more thereof, preferably from the group consisting of water, C1-C4 alcohols, C1-C3 ketones, and a combination of two or more thereof, wherein more preferably, the at least one solvent comprises, more preferably consists of, water and a C1-C4 alcohol, preferably water and ethanol, or comprises, more preferably consists of, acetone.
60. The process of embodiment 58 or 59, wherein the rapid-drying is carried out by spray-drying or spray-granulation, preferably by spray-drying.
61. The process of embodiment 60, wherein the spray-drying is carried out at an inlet temperature in the range of from 50 to 100° C., and at an outlet temperature in the range of from 20 to 70° C.
62. A process for the preparation of sofosbuvir of which at least 95 weight-%, preferably at least 99 weight-%, more preferably at least 99.9 weight-% are present in its amorphous form, comprising
   (i) providing sofosbuvir in at least one crystalline form or in amorphous form or as a mixture of at least one crystalline form and amorphous form, preferably providing sofosbuvir of which at least 95 weight-%, preferably at least 99 weight-%, more preferably at least 99.9 weight-% are present in at least one crystalline form;
   (ii) subjecting the sofosbuvir provided in (i) to a melt method, preferably a hot-melt method, more preferably a hot-melt extrusion method, obtaining the sofosbuvir of which at least 95 weight-%, preferably at least 99 weight-%, more preferably at least 99.9 weight-% are present in its amorphous form.

The present invention is further illustrated by the following reference examples, examples, and comparative examples.

REFERENCE EXAMPLE 1: DETERMINATION OF THE PH OF THE SILICON-BASED INORGANIC ADSORBENTS

To 400 mg of a given silicon-based inorganic adsorbent, 10 mL of DI (de-ionized) water were added at room temperature. After stirring for 2 minutes, the mixture was allowed to stand for 2 minutes at room temperature. Then, the pH of the aqueous phase was determined using pH meter.

REFERENCE EXAMPLE 2: PREPARATION AND CHARACTERIZATION OF AMORPHOUS SOFOSBUVIR 2.1 Preparation by Spray-Drying Amorphous sofosbuvir can be prepared according to the following recipe: 1.0 g of sofosbuvir crystalline Form 1 prepared according to WO 2011/123645 A, Example 10, is dissolved in 20 ml acetone. The solution is spray-dried through the nozzle of a Büchi Spray Dryer (inlet temperature: 60-72° C., outlet temperature: 35-45° C., spray rate of feed: 3-5 ml/min), yielding amorphous sofosbuvir.

2.2 Preparation by Lyophilization

Amorphous sofosbuvir was prepared according to the following recipe: To 400 mg of sofosbuvir crystalline Form 1 prepared according to WO 2011/123645 A, Example 10, 3.5 mL ethanol were added, followed by 12 mL DI water. The mixture was subjected to sonication (2 to 5 minutes at room temperature in a VWR Ultrasonic Cleaner apparatus) to accelerate the dissolution of the solid material. The homogeneous solution was frozen in a bath of liquid nitrogen and lyophilized at −36° C. at a pressure of from 0 to 2 mbar, yielding amorphous sofosbuvir.

2.3 Characterization

Figure 15:
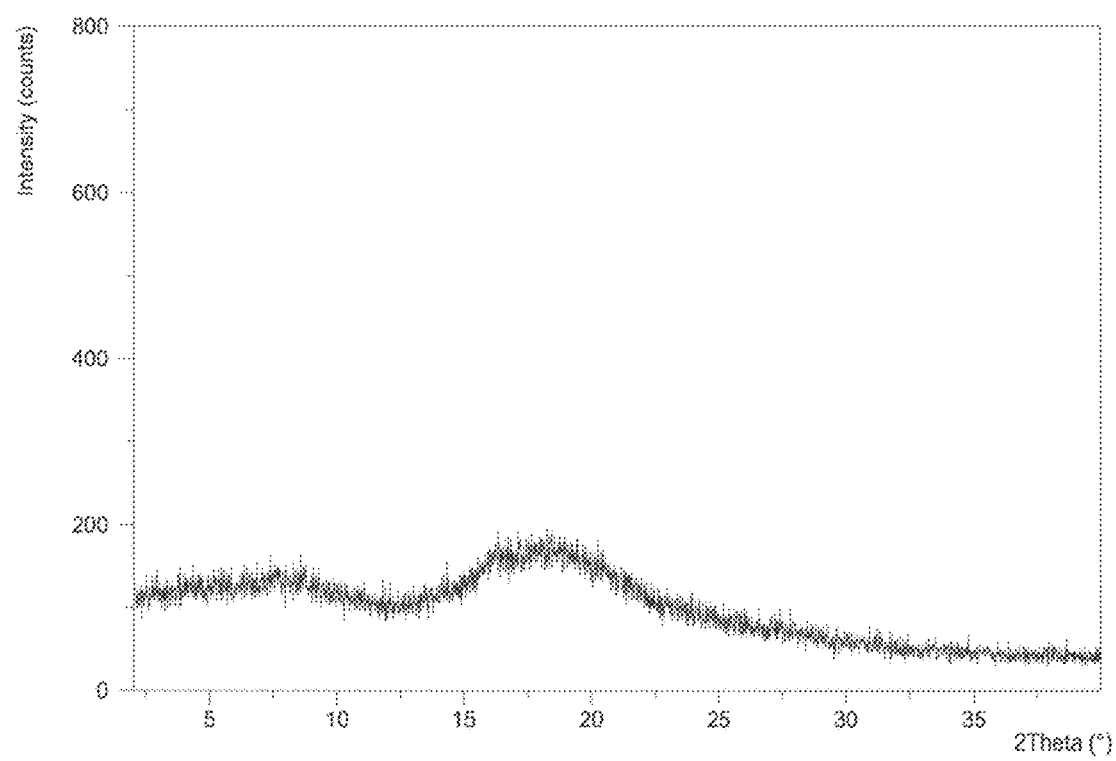

The sofosbuvir obtained according to Reference Example 2.2 above was subjected to XRD analysis as follows: the X-ray powder diffraction pattern (XRPD) was obtained with a PANalytical X'Pert PRO diffractometer equipped with a theta/theta coupled goniometer in transmission geometry, programmable XYZ stage with well plate holder, Cu-Kalpha1,2 radiation (wavelength 0.15419 nm) with a focusing mirror and a solid state PIXcel detector. The patterns were recorded at a tube voltage of 45 kV and a tube current of 40 mA, applying a step size of 0.013° 2-theta with 40 s per step (255 channels) in the angular range of 2° to 40° 2-theta at ambient conditions. The XRD is shown in FIG. 15.

REFERENCE EXAMPLE 3: DETERMINATION OF THE MOISTURE STABILITY 25-30 mg of a given solid composition prepared according to the Examples and Comparative Examples below were exposed to an atmosphere having a relative humidity of 75% and a temperature of 40° C. for a period of time as indicated in Table 1 below and, if stable and if not having deliquesced, analysed via XRD as described in Reference Example 2.3 with respect to the amorphousness.

REFERENCE EXAMPLE 4: DYNAMIC VAPOR SORPTION (DVS) MEASUREMENTS—DETERMINATION OF ∆M(DESORPTION) AND ∆M(ADSORPTION) AT 75% RELATIVE Humidity and 25° C.

The adsorption-desorption isotherms from which the values of ∆m(desorption) and ∆m(adsorption) at 75% relative humidity and at 25° C. were obtained, were recorded with an SPSx-1µ (1 micro) moisture sorption analyzer (ProUmid GmbH & Co. KG, Ulm, Germany).

A given measurement cycle was started at ambient relative humidity (r.h.), in the present case 40% r.h. The r.h. was decreased to 3% and then to 0%. For this isotherm, as black filled square with a white x inside is used in the respective Figures. Subsequently, the adsorption isotherm was recorded, i.e. r.h. was increased to 5%, then to 10%, and thereafter in 10% steps. Once having reached the chosen maximum r.h. value, the desorption isotherm was recorded, starting with 10% steps down to a r.h. of 10%, followed by a r.h. decrease in 5% steps to 0% r.h. The last step consisted of increasing the r.h. to ambient r.h. As to the isotherm obtained by the last step, a black filled square with a white asterix inside is used as symbol in the respective Figures. The time per step was set to 3 to 5 hours. For all steps and all isotherms, the temperature was set to 25±0.1° C.

To obtain the ∆m(desorption) and ∆m(adsorption) values, the recorded adsorption-desorption isotherms shown in the Figures of the present invention were analysed by comparing the value of ∆m(desorption), plotted on the y axis, of a given desorption isotherm with the value of ∆m(adsorption), plotted on the y axis, of the respective adsorption isotherm, both at 75% r.h., plotted on the x axis.

EXAMPLE 1: PREPARATION OF A SOLID DISPERSION COMPRISING AMORPHOUS SOFOSBUVIR AND A HYDROPHILIC WATER-SOLUBLE POLYMER AS THE MATRIX COMPOUND

Figure 2:
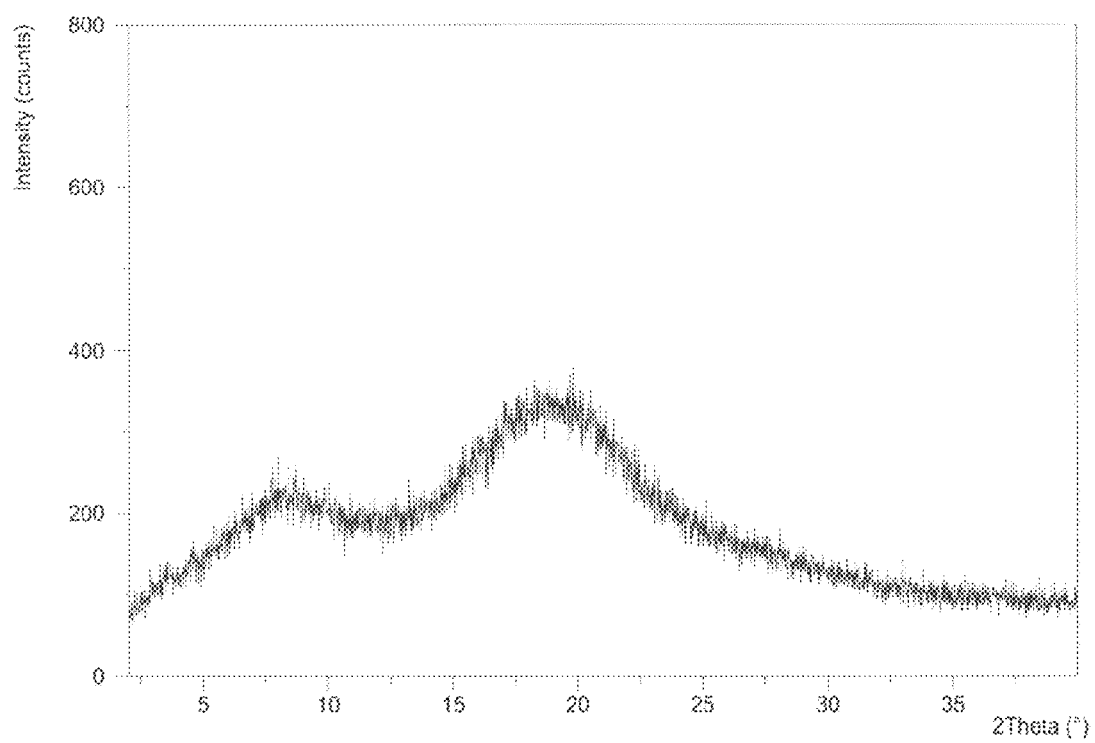

E1.1 To 181 mg sofosbuvir crystalline Form 1 prepared according to WO 2011/123645 A, Example 10, and 45 mg hydroxypropylmethylcellulose (HPMC E5, having an average $M_w$ of 10 000 g/mol; commercially available from Dow Chemical Co. under the trade name Methocel E5), 4 mL ethanol were added, followed by 12 mL DI water. The mixture was subjected to sonication (2 to 5 minutes in a VWR Ultrasonic Cleaner apparatus) to accelerate the dissolution of the solids. The homogeneous solution was frozen in a bath of liquid nitrogen and lyophilized at a temperature of from –40° C. to –30° C. at a pressure of from 0 to 2 mbar. The resulting solid dispersion was subjected to a moisture stability test according to Reference Example 3. The results are summarized in Table 1 below. The X-ray powder diffractogram (XRPD) of the solid dispersion stored at ambient conditions is shown in FIG. 1, the XRPD of the solid dispersion after the stress test is shown in FIG. 2. FIGS. 1 and 2 show that the sofosbuvir comprised in the solid dispersion did not crystallize during the moisture stability test.

E1.2 To 150 mg sofosbuvir crystalline Form 1 prepared according to WO 2011/123645 A, Example 10, and 50 mg hydroxypropylmethylcellulose (HPMC E15, having an average molecular weight $M_w$ of 17000 g/mol; commercially available from Dow Chemical Co. under the trade name Methocel E15), 4 mL ethanol were added, followed by 12 ml, DI water. The mixture was subjected to sonication (2 to 5 minutes in a VWR Ultrasonic Cleaner apparatus) to accelerate the dissolution of the solids. The homogeneous solution was frozen in a bath of liquid nitrogen and lyophilized at a temperature of from –40° C. to –30° C. at a pressure of from 0 to 2 mbar. The resulting solid dispersion was subjected to a moisture stability test according to Reference Example 3. The results are summarized in Table 1 below.

EXAMPLE 2: PREPARATION OF A SOLID DISPERSION COMPRISING AMORPHOUS SOFOSBUVIR AND A SILICON-BASED INORGANIC ADSORBENT AS THE MATRIX COMPOUND

Figure 3:
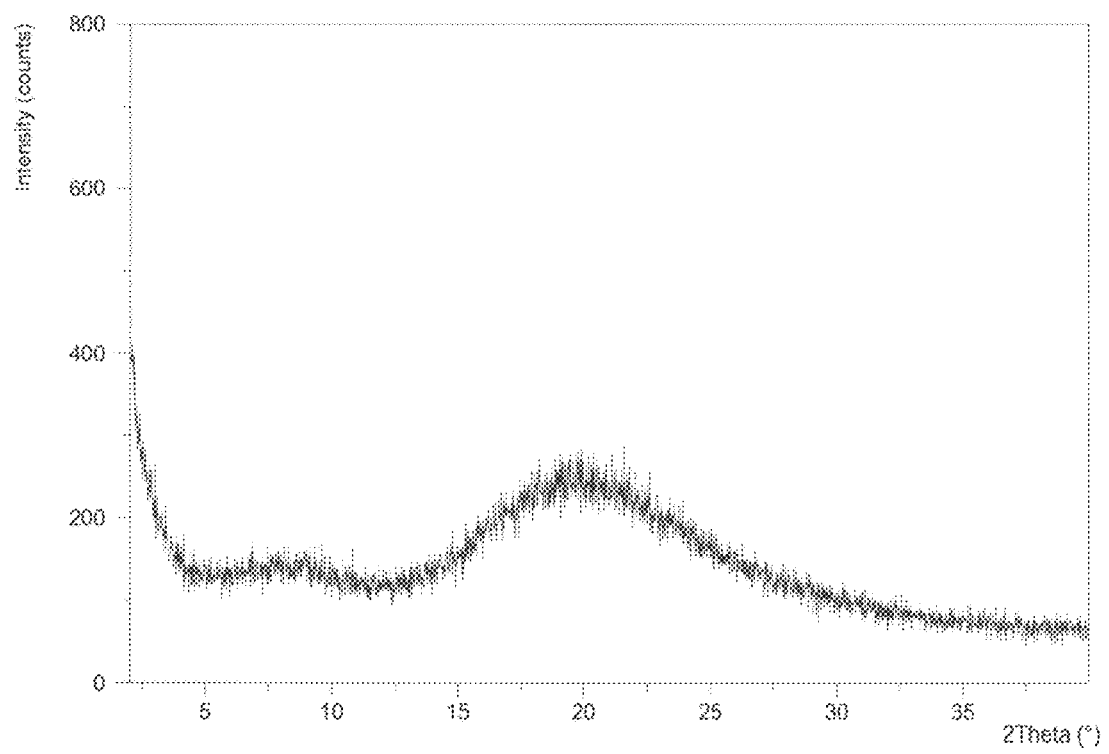
Figure 4:
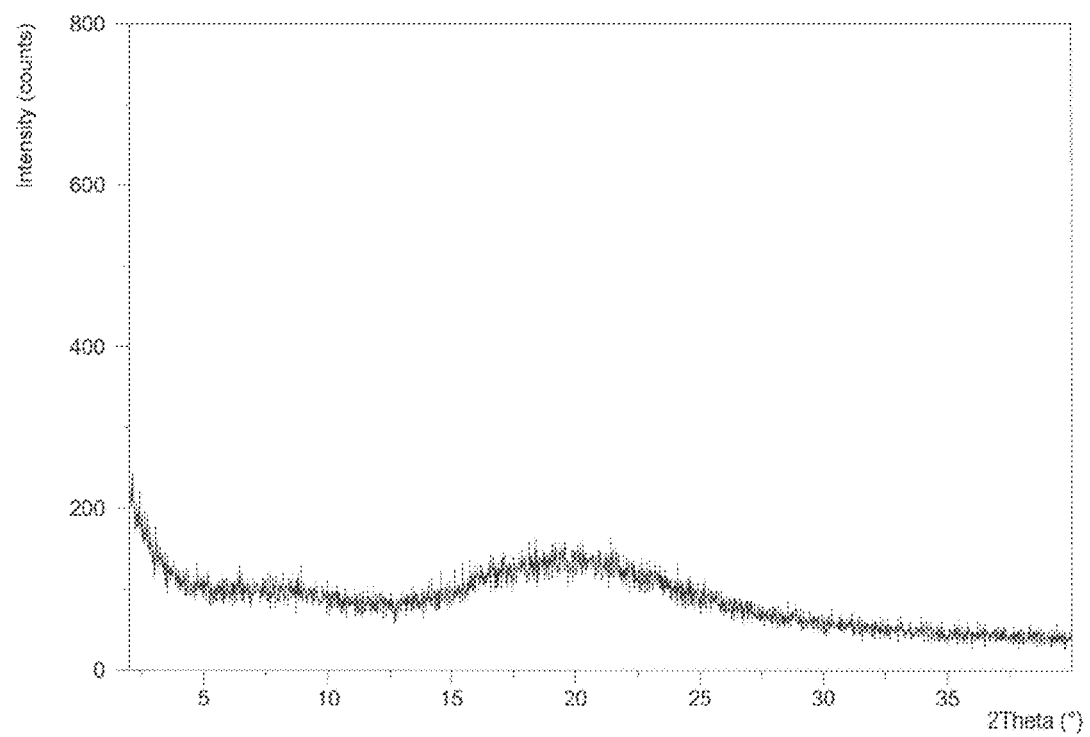

E2.1 800 mg sofosbuvir crystalline Form 1 prepared according to WO 2011/123645 A, Example 10, were dissolved in 16 mL acetone. 3 mL of the sofosbuvir solution in acetone were added to 50 mg Syloid® 72 FP having a pH of 7.5 (a synthetic amorphous silica; from Grace). The solvent was evaporated in a rotary evaporator at 40° C., and the solid residue was dried under vacuum at a pressure of from 20 to 30 mbar and room temperature for 18 h. The resulting solid dispersion was subjected to a moisture stability test according to Reference Example 3. The results are summarized in Table 1 below. The X-ray powder diffractogram (XRPD) of the solid dispersion stored at ambient conditions is shown in FIG. 3, the XRPD of the solid dispersion after the stress test is shown in FIG. 4. FIGS. 3 and 4 show that the sofosbuvir comprised in the solid dispersion did not crystallize during the moisture stability test.

E2.2 800 mg sofosbuvir crystalline Form 1 prepared according to WO 2011/123645 A, Example 10, were dissolved in 16 mL acetone. 3 mL of the sofosbuvir solution in acetone were added to 50 mg Syloid® 244 FP having a pH of 7.6 (a synthetic amorphous silica; from Grace). The solvent was evaporated in a rotary evaporator at 40° C., and the solid residue was dried under vacuum at a pressure of from 20 to 30 mbar and room temperature for 18 h. The resulting solid dispersion was subjected to a moisture stability test according to Reference Example 3. The results are summarized in Table 1 below.

E2.3 800 mg sofosbuvir crystalline Form 1 prepared according to WO 2011/123645 A, Example 10, were dissolved in 16 mL acetone. 3 mL of the sofosbuvir solution in acetone were added to 50 mg Neusilin® UFL2 having a pH of 7.4 (an amorphous synthetic magnesium aluminosilicate; from Fuji Chemical Industry Col., Ltd.). The solvent was evaporated in a rotary evaporator at 40° C., and the solid residue was dried under vacuum at a pressure of from 20 to 30 mbar and room temperature for 18 h. The resulting solid dispersion was subjected to a moisture stability test according to Reference Example 3. The results are summarized in Table 1 below.

E2.4 800 mg sofosbuvir crystalline Form 1 prepared according to WO 2011/123645 A, Example 10, were dissolved in 16 mL acetone. 3 mL of the sofosbuvir solution in acetone were added to 50 mg Neusilin® US2 having a pH of 7.1 (an amorphous synthetic magnesium aluminosilicate; from Fuji Chemical Industry Col., Ltd.). The solvent was evaporated in a rotary evaporator at 40° C., and the solid residue was dried under vacuum at a pressure of from 20 to 30 mbar and room temperature for 18 h. The resulting solid dispersion was subjected to a moisture stability test according to Reference Example 3. The results are summarized in Table 1 below.

COMPARATIVE EXAMPLE 1: PREPARATION OF A SOLID DISPERSION COMPRISING AMORPHOUS SOFOSBUVIR AND A HYDROPHILIC WATER-SOLUBLE POLYMER AS THE MATRIX COMPOUND

CE1.1 Comparative Example 1 was carried out as Example 1. Instead of HPMC E5, hydroxypropylcellulose was used (HPC; commercially available under the tradename Klucel® LF, from Ashland Inc.). The resulting solid dispersion was subjected to a moisture stability test according to Reference Example 3. The results are summarized in Table 1 below.

CE1.2 Comparative Example 1 was carried out as Example 1. Instead of HPMC E5, polyvinylpyrrolidone was used (PVP 40; commercially available from Sigma-Aldrich). The resulting solid dispersion was subjected to a moisture stability test according to Reference Example 3. The results are summarized in Table 1 below.

CE1.3 Comparative Example 1 was carried out as Example 1. Instead of HPMC E5, a polyvinyl caprolactam-polyvinyl acetate-polyethylene glycol graft copolymer was used (Soluplus®; commercially available from BASF SE). The resulting solid dispersion was subjected to a moisture stability test according to Reference Example 3. The results are summarized in Table 1 below.

COMPARATIVE EXAMPLE 2: PREPARATION OF A SOLID DISPERSION COMPRISING AMORPHOUS SOFOSBUVIR AND A SILICON-BASED INORGANIC ADSORBENT AS THE MATRIX COMPOUND

CE2.1 Comparative Example 2.1 was carried out as Example 2.1. Instead of Syloid® 72 FP having a pH of 7.5, Syloid® AL-1 FP having a pH of 5.7 was used (a synthetic amorphous silica; from Grace). The resulting solid dispersion was subjected to a moisture stability test according to Reference Example 3. The results are summarized in Table 1 below.

TABLE 1

Stability of the solid dispersions of the Examples and Comparative Examples - $\Delta\Delta m/\% = \Delta m(desorption)/\% - \Delta m(adsorption)/\%$

| | matrix compound | | composition having a sofosbuvir content of 75 weight-%/state of composition/state of sofosbuvir | |
|---|---|---|---|---|
| example | compound | $\Delta\Delta m/\%$ | after preparation | after 8 weeks at 40° C./75% r.h. |
| E1.1 | HPMC E5 | ≥0 | solid/amorphous | solid/amorphous |
| E1.2 | HPMC E15 | ≥0 | solid/amorphous | solid/amorphous |
| E2.1 | Syloid ® 72 FP | ≥0 | solid/amorphous | solid/amorphous |
| E2.2 | Syloid ® 244 FP | ≥0 | solid/amorphous | solid/amorphous |
| E2.3 | Neusilin ® UFL2 | ≥0 | solid/amorphous | solid/amorphous |
| E2.4 | Neusilin ® US2 | ≥0 | solid/amorphous | solid/amorphous |
| CE1.1 | HPC, Klucel ® LF | <0 | solid/amorphous | deliquescence/— |
| CE1.2 | PVP 40 | <0 | solid/amorphous | deliquescence/— |
| CE1.3 | Soluplus | <0 | solid/amorphous | deliquescence/— |
| CE2.1 | Syloid ® AL-1 FP | <0 | solid/amorphous | deliquescence/— |

The results of the stability tests as shown in Table 1 above clearly show that the matrix compounds having a $\Delta\Delta m$ value of ≥0%, in particular the matrix compounds having a $\Delta\Delta m$ value of ≥0% selected from the group consisting of hydrophilic water-soluble polymers and silicon-based inorganic adsorbents stabilize amorphous sofosbuvir in the solid composition, even after the stress conditions of 8 weeks at 40° C. in an atmosphere of a relative humidity of 75%. On the other hand, matrix compounds which do not fulfill the requirement of $\Delta\Delta m≥0\%$, do not exhibit the advantageous effect of stabilizing amorphous sofosbuvir in the solid composition after the stress conditions of 8 weeks at 40° C. in an atmosphere of a relative humidity of 75%, regardless if the matrix compound is, for example, a water-soluble polymer (comparative examples CE1.1, CE1.2, CE1.3) or a silicon-based inorganic adsorbent (comparative example CE2.1).

SHORT DESCRIPTION OF THE FIGURES

FIG. 1 shows the XRPD of the solid dispersion according to Example E1.1 after preparation, prior to the moisture stability test according to Reference Example 3. The parameters of the XRPD measurement are identical to those described in Reference Example 2.3. The x axis shows the 2 theta/° values, with tick marks, from left to right, at 5, 10, 15, 20, 25, and 35. The y axis shows the intensity in counts, with tick marks, from bottom to top, at 0, 200, 400, 600, and 800.

FIG. 2 shows the XRPD of the solid dispersion according to Example E1.2 after the moisture stability test according to Reference Example 3. The parameters of the XRPD measurement are identical to those described in Reference Example 2.3. The x axis shows the 2 theta/° values, with tick marks, from left to right, at 5, 10, 15, 20, 25, and 35. The y axis shows the intensity in counts, with tick marks, from bottom to top, at, 0, 200, 400, 600, and 800.

FIG. 3 shows the XRPD of the solid dispersion according to Example E2.1 after preparation, prior to the moisture stability test according to Reference Example 3. The parameters of the XRPD measurement are identical to those described in Reference Example 2.3. The x axis shows the 2 theta/° values, with tick marks, from left to right, at 5, 10, 15, 20, 25, and 35. The y axis shows the intensity in counts, with tick marks, from bottom to top, at 0, 200, 400, 600, and 800.

FIG. 4 shows the XRPD of the solid dispersion according to Example E2.2 after the moisture stability test according to Reference Example 3. The parameters of the XRPD measurement are identical to those described in Reference Example 2.3. The x axis shows the 2 theta/° values, with tick marks, from left to right, at 5, 10, 15, 20, 25, and 35. The y axis shows the intensity in counts, with tick marks, from bottom to top, at 0, 200, 400, 600, and 800.

Figure 5:
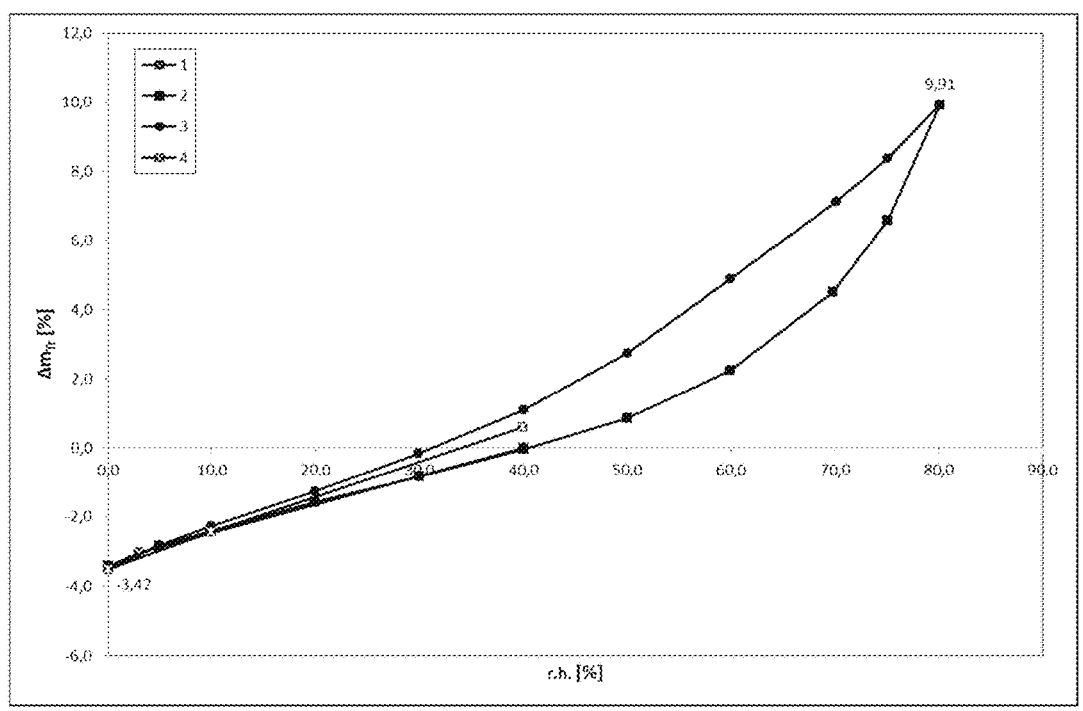

FIG. 5 shows the DVS isotherm of the matrix compound HPMC E5 (example E1.1), recorded as described in Reference Example 4. The x axis shows the r.h. (relative humidity, in %) values, with tick marks at 0,0; 10,0; 20,0; 30,0; 40,0; 50,0; 60,0; 70,0; 80,0; and 90,0. The y axis shows the $\Delta m$ values (in %), with tick marks, from bottom to top, at −6,0; −4,0; −2,0; 0,0; 2,0; 4,0; 6,0; 8,0; 10,0; and 12,0. The $\Delta m$(desorption) values are obtained from the desorption isotherm (symbols: ●), the $\Delta m$(adsorption) values are obtained from the adsorption isotherm (symbols: ■).

Figure 6:
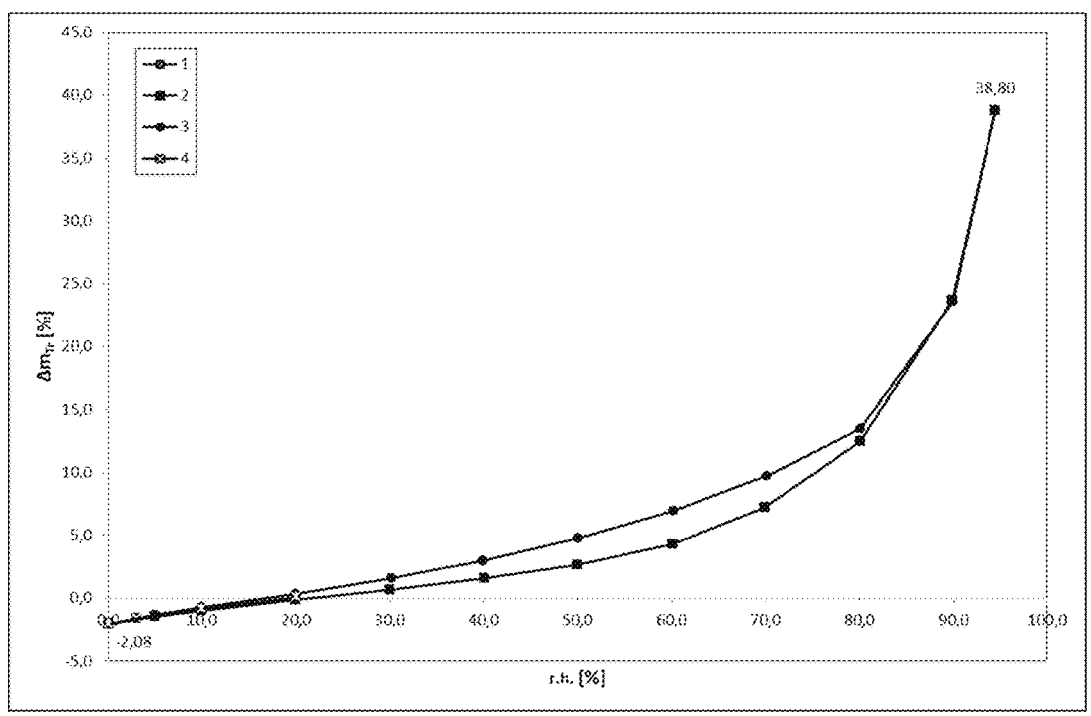

FIG. 6 shows the DVS isotherm of the matrix compound HPMC E15 (example E1.2), recorded as described in Reference Example 4. The x axis shows the r.h. (relative humidity, in %) values, with tick marks, from left to right, at 0,0; 10,0; 20,0; 30,0; 40,0; 50,0; 60,0; 70,0; 80,0; 90,0; and 100,0. The y axis shows the $\Delta m$ values (in %), with tick marks, from bottom to top, at −5,0; 0,0; 5,0; 10,0; 15,0; 20,0; 25,0; 30,0; 35,0; 40,0; and 45,0. The Δm(desorption) values are obtained from the desorption isotherm (symbols: ●), the Δm(adsorption) values are obtained from the adsorption isotherm (symbols: ■).

Figure 7:
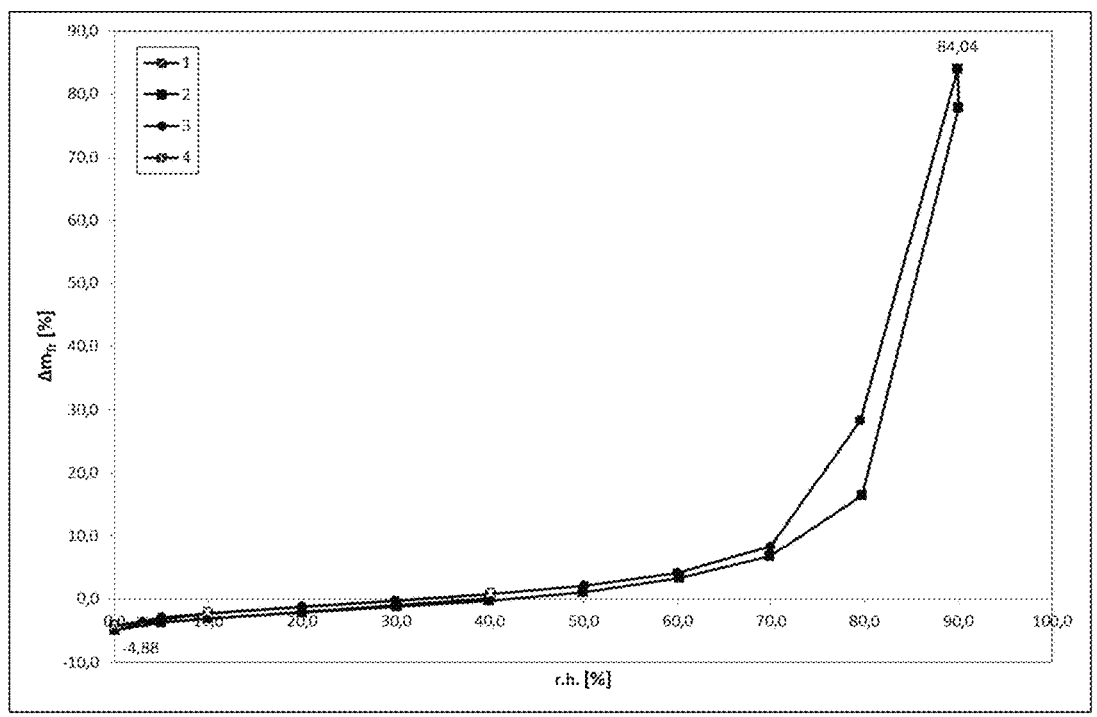

FIG. 7 shows the DVS isotherm of the matrix compound Syloid® 72 FP (example E2.1), recorded as described in Reference Example 4. The x axis shows the r.h. (relative humidity, in %) values, with tick marks, from left to right, at 0,0; 10,0; 20,0; 30,0; 40,0; 50,0; 60,0; 70,0; 80,0; 90,0; and 100,0. The y axis shows the Δm values (in %), with tick marks, from bottom to top, at −10,0; 0,0; 10,0; 20,0; 30,0; 40,0; 50,0; 60,0; 70,0; 80,0; and 90,0. The Δm(desorption) values are obtained from the desorption isotherm (symbols: ●), the Δm(adsorption) values are obtained from the adsorption isotherm (symbols: ■).

Figure 8:
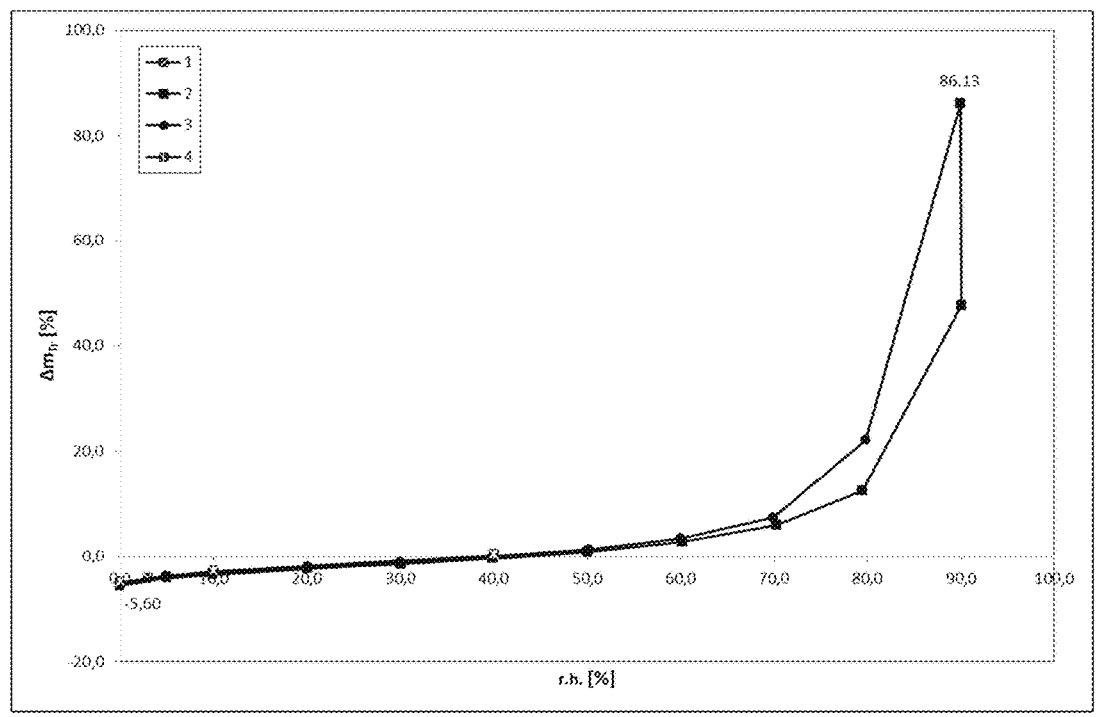

FIG. 8 shows the DVS isotherm of the matrix compound Syloid® 244 FP (example E2.2), recorded as described in Reference Example 4. The x axis shows the r.h. (relative humidity, in %) values, with tick marks, from left to right, at 0,0; 10,0; 20,0; 30,0; 40,0; 50,0; 60,0; 70,0; 80,0; 90,0; and 100,0. The y axis shows the Δm values (in %), with tick marks, from bottom to top, at −20,0; 0,0; 20,0; 40,0; 60,0; 80,0; and 100,0. The Δm(desorption) values are obtained from the desorption isotherm (symbols: ●), the Δm(adsorption) values are obtained from the adsorption isotherm (symbols: ■).

Figure 9:
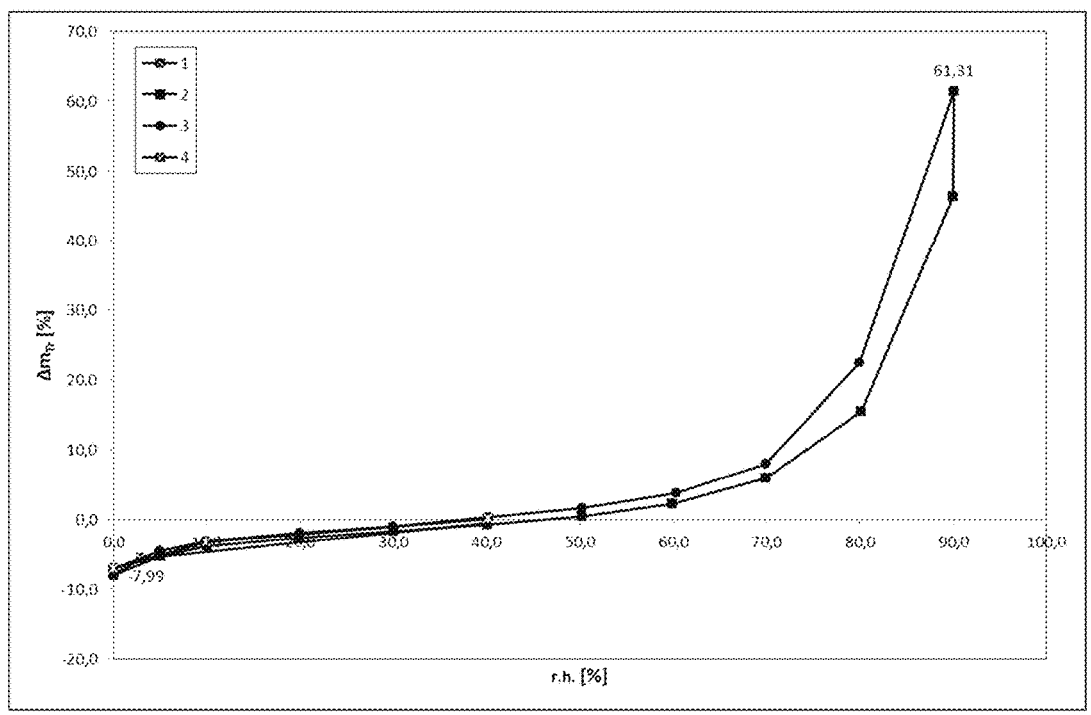

FIG. 9 shows the DVS isotherm of the matrix compound Neusilin® UFL2 (example E2.3), recorded as described in Reference Example 4. The x axis shows the r.h. (relative humidity, in %) values, with tick marks, from left to right, at 0,0; 10,0; 20,0; 30,0; 40,0; 50,0; 60,0; 70,0; 80,0; 90,0; and 100,0. The y axis shows the Δm values (in %), with tick marks, from bottom to top, at −20,0; −10,0; 0,0; 10,0; 20,0; 30,0; 40,0; 50,0; 60,0; and 70,0. The Δm(desorption) values are obtained from the desorption isotherm (symbols: ●), the Δm(adsorption) values are obtained from the adsorption isotherm (symbols: ■).

Figure 10:
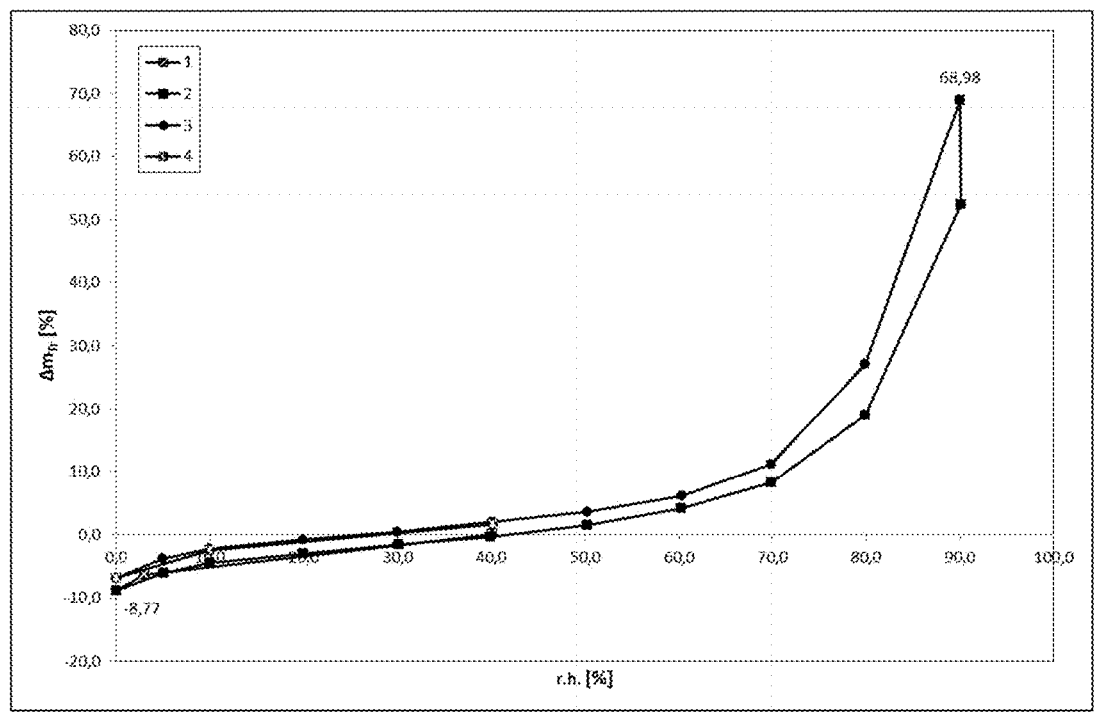

FIG. 10 shows the DVS isotherm of the matrix compound Neusilin® US2 (example E2.4), recorded as described in Reference Example 4. The x axis shows the r.h. (relative humidity, in %) values, with tick marks, from left to right, at 0,0; 10,0; 20,0; 30,0; 40,0; 50,0; 60,0; 70,0; 80,0; 90,0; and 100,0. The y axis shows the Δm values (in %), with tick marks, from bottom to top, at −20,0; −10,0; 0,0; 10,0; 20,0; 30,0; 40,0; 50,0; 60,0; 70,0; and 80,0. The Δm(desorption) values are obtained from the desorption isotherm (symbols: ●), the Δm(adsorption) values are obtained from the adsorption isotherm (symbols: ■).

Figure 11:
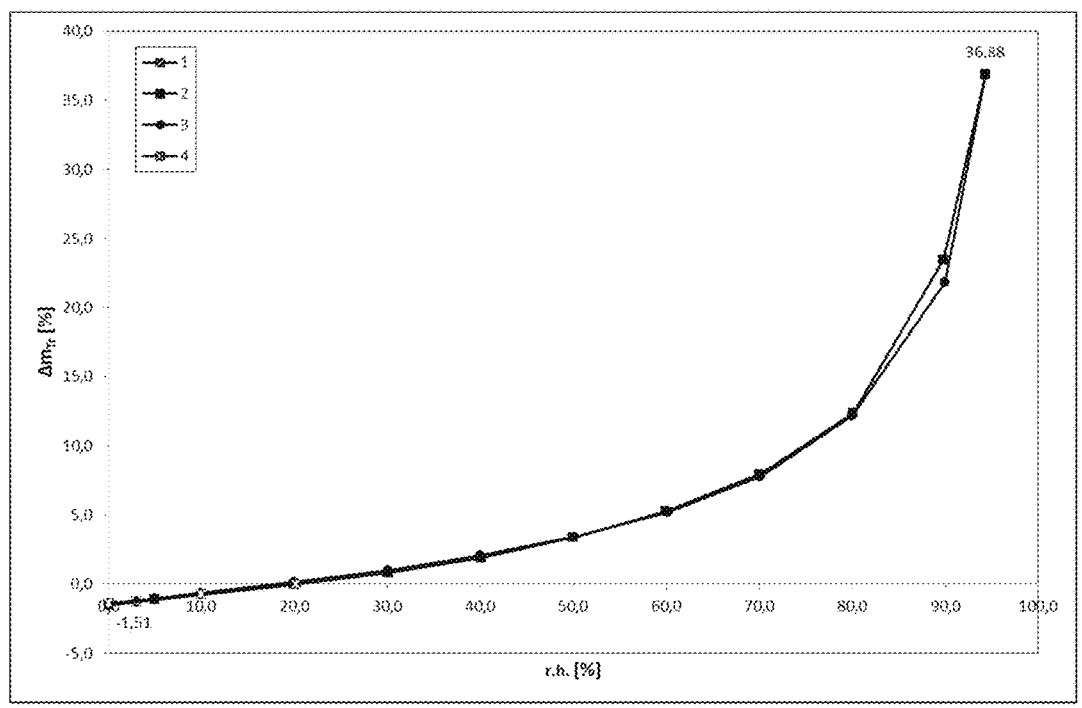

FIG. 11 shows the DVS isotherm of the matrix compound HPC, Klucel® LF (comparative example CE1.1), recorded as described in Reference Example 4. The x axis shows the r.h. (relative humidity, in %) values, with tick marks, from left to right, at 0,0; 10,0; 20,0; 30,0; 40,0; 50,0; 60,0; 70,0; 80,0; 90,0; and 100,0. The y axis shows the Δm values (in %), with tick marks, from bottom to top, at −5,0; 0,0; 5,0; 10,0; 15,0; 20,0; 25,0; 30,0; 35,0; and 40,0. The Δm(desorption) values are obtained from the desorption isotherm (symbols: ●), the Δm(adsorption) values are obtained from the adsorption isotherm (symbols: ■). At 75% r.h., the value of Δm(desorption) is 10.0%, the value of Δm(adsorption) is 10.2%; therefore, the ΔΔm value as defined in Table 1 is −0.2 and, thus, <0.

Figure 12:
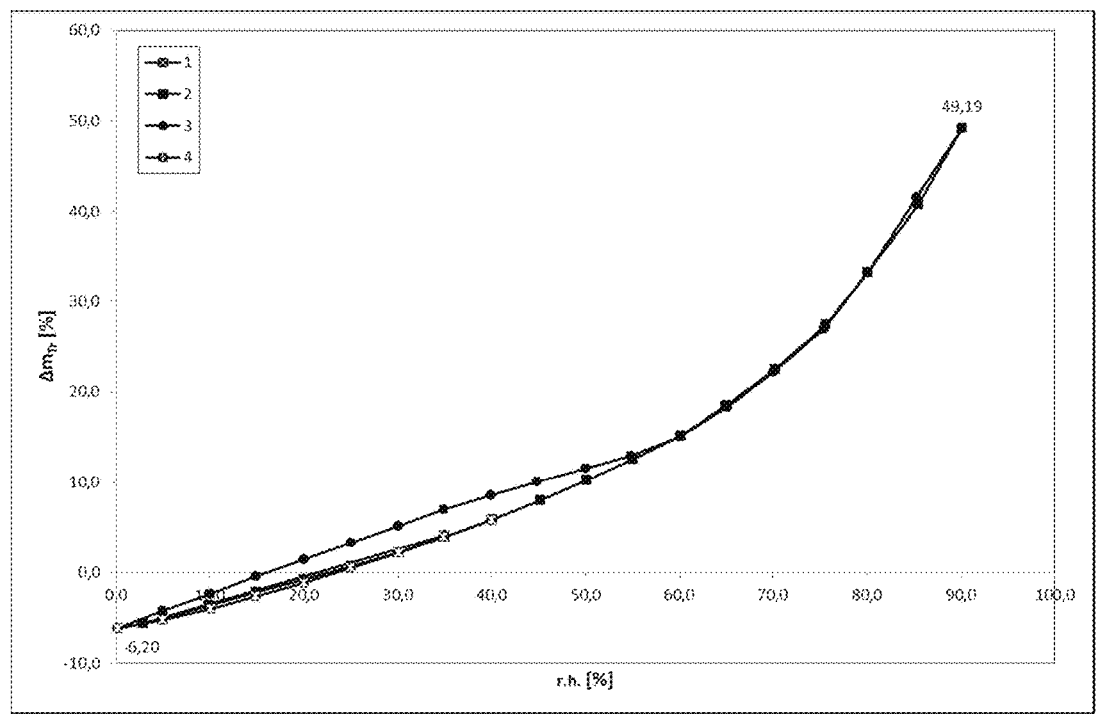

FIG. 12 shows the DVS isotherm of the matrix compound PVP 40 (comparative example CE1.2), recorded as described in Reference Example 4. The x axis shows the r.h. (relative humidity, in %) values, with tick marks, from left to right, at 0,0; 10,0; 20,0; 30,0; 40,0; 50,0; 60,0; 70,0; 80,0; 90,0; and 100,0. The y axis shows the Δm values (in %), with tick marks, from bottom to top, at −10,0; 0,0; 10,0; 20,0; 30,0; 40,0; 50,0; and 60,0. The Δm(desorption) values are obtained from the desorption isotherm (symbols: ●), the Δm(adsorption) values are obtained from the adsorption isotherm (symbols: ■).

At 75% r.h., the value of Δm(desorption) is 26.9%, the value of Δm(adsorption) is 27.4%; therefore, the ΔΔm value as defined in Table 1 is −0.5 and, thus, <0.

Figure 13:
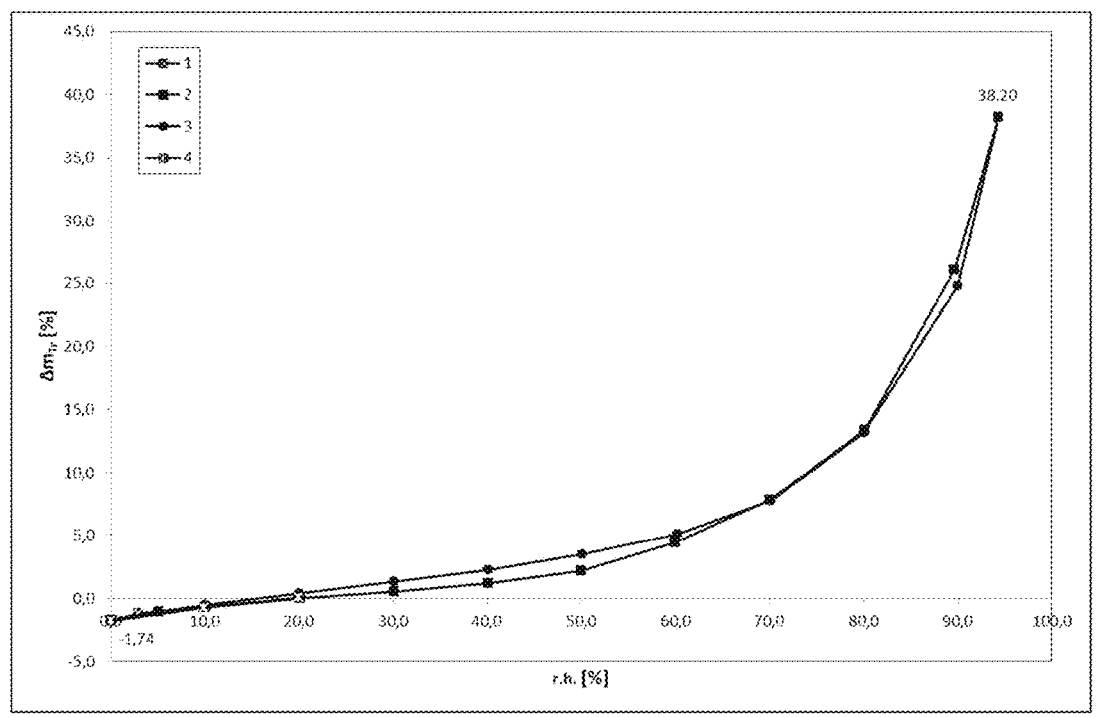

FIG. 13 shows the DVS isotherm of the matrix compound Soluplus (comparative example CE1.3), recorded as described in Reference Example 4. The x axis shows the r.h. (relative humidity, in %) values, with tick marks, from left to right, at 0,0; 10,0; 20,0; 30,0; 40,0; 50,0; 60,0; 70,0; 80,0; 90,0; and 100,0. The y axis shows the Δm values (in %), with tick marks, from bottom to top, at −5,0; 0,0; 5,0; 10,0; 15,0; 20,0; 25,0; 30,0; 35,0; 40,0; and 45,0. The Δm(desorption) values are obtained from the desorption isotherm (symbols: ●), the Δm(adsorption) values are obtained from the adsorption isotherm (symbols: ■).

At 75% r.h., the value of Δm(desorption) is 10.4%, the value of Δm(adsorption) is 10.6%; therefore, the ΔΔm value as defined in Table 1 is −0.2 and, thus, <0.

Figure 14:
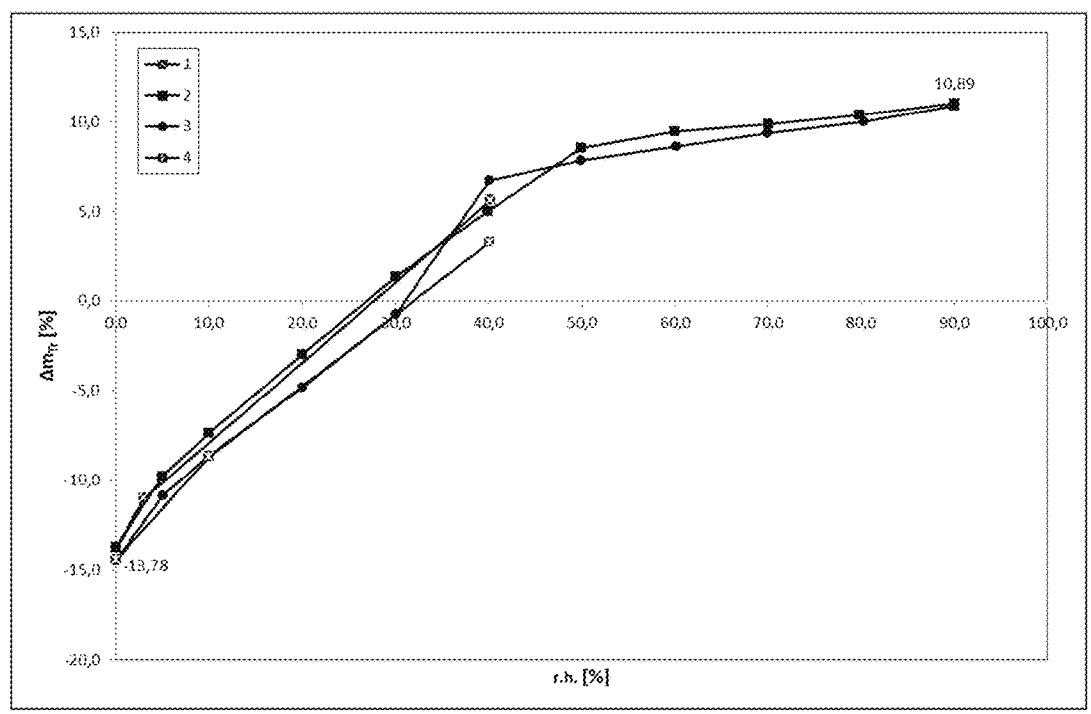

FIG. 14 shows the DVS isotherm of the matrix compound Syloid® AL-1 FP (comparative example CE2.1), recorded as described in Reference Example 4. The x axis shows the r.h. (relative humidity, in %) values, with tick marks, from left to right, at 0,0; 10,0; 20,0; 30,0; 40,0; 50,0; 60,0; 70,0; 80,0; 90,0; and 100,0. The y axis shows the Δm values (in %), with tick marks, from bottom to top, at −20,0; −15,0; −10,0; −5,0; 0,0; 5,0; 10,0; and 15,0. The Δm(desorption) values are obtained from the desorption isotherm (symbols: ●), the Δm(adsorption) values are obtained from the adsorption isotherm (symbols: ■).

FIG. 15 shows the XRPD of the amorphous sofosbuvir prepared according to Reference Example 2.2. The measurement parameters are given in Reference Example 2.3. The parameters of the XRPD measurement are identical to those described in Reference Example 2.3. The x axis shows the 2 theta/° values, with tick marks, from left to right, at 5, 10, 15, 20, 25, and 35. The y axis shows the intensity in counts, with tick marks, from bottom to top, at 0, 200, 400, 600, and 800.

CITED PRIOR ART

WO 2010/135569 A
WO 2013/101550 A
WO 2011/123645 A

The invention claimed is:

1. A solid composition comprising sofosbuvir according to formula (I)

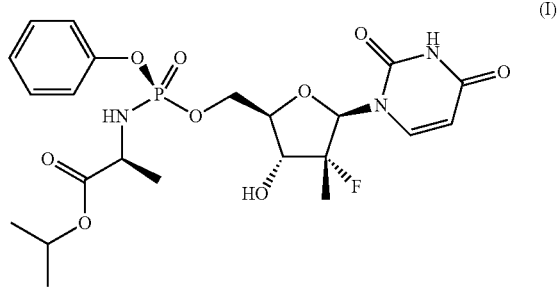 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

and at least one pharmaceutically acceptable matrix compound wherein at least 99 weight-% of the sofosbuvir comprised in the composition are present in amorphous form, at least 99 weight-% of the solid composition consist of the sofosbuvir and the at least one matrix compound, and wherein the solid composition contains the sofosbuvir in an amount of at least 55 weight-% based on the combined weight of the sofosbuvir and the at least one matrix compound, wherein in the adsorption-desorption isotherm of the at least one pharmaceutically acceptable matrix compound, the mass difference Δm (desorption) at 75% relative humidity and 25° C. is greater than or equal to the mass difference Δm (adsorption) at 75% relative humidity and 25° C. determined according to dynamic vapor sorption measurement wherein the at least one matrix compound is selected from the group consisting of hydrophilic water-soluble polymers, silicon-based inorganic adsorbents and a combination of two or more thereof and wherein the weight ratio of the sofosbuvir and the matrix compound is from 6:4 to 8.5:1.5.

2. The solid composition of claim 1, containing the sofosbuvir in an amount in the range of from 55 to 90 weight-% based on the combined weight of the sofosbuvir and the at least one matrix compound.

3. The solid composition of claim 1, wherein the at least one matrix compound comprises at least one silicon-based inorganic adsorbent.

4. The solid composition of claim 3, wherein the at least one matrix compound has a pH in the range of from 6.0 to 9.0.

5. The solid composition of claim 1, wherein the at least one matrix compound comprises at least one hydrophilic water-soluble polymer.

6. The solid composition of claim 1, wherein at least 99.5 weight-% of the sofosbuvir comprised in the composition are present in amorphous form and wherein at least 99.5 weight-% of the solid composition consist of the sofosbuvir and the at least one matrix compound.

7. The solid composition of claim 1, comprising less than 0.1 weight-% of a surfactant.

8. The solid composition of claim 1, having a moisture stability of at least 95% wherein the moisture stability is defined as the amount of solid amorphous sofosbuvir which is present in the solid composition after having been exposed to a relative humidity of 75% at 40° C. for 8 weeks, relative to the amount of solid amorphous sofosbuvir which is present in the solid composition before said exposure.

9. The solid composition of claim 1, being a solid dispersion.

10. A pharmaceutical composition comprising the solid composition according to claim 1.

11. A process for the preparation of a solid composition, comprising sofosbuvir according to formula (I)

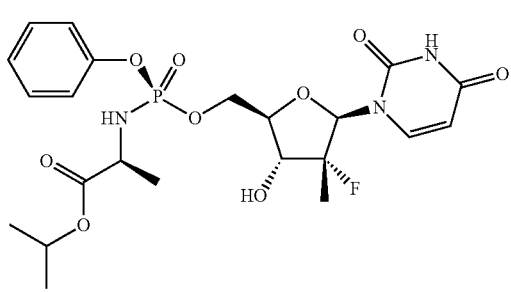

and at least one pharmaceutically acceptable matrix compound, said process comprising embedding sofosbuvir in a matrix consisting of the at least one pharmaceutically acceptable matrix compound, starting from a solution of the sofosbuvir in at least one solvent, wherein at least 99 weight-% of the sofosbuvir comprised in the composition are present in amorphous form, at least 99 weight-% of the solid composition consist of the sofosbuvir and the at least one matrix compound, and wherein the solid composition contains the sofosbuvir in an amount of at least 55 weight-% based on the combined weight of the sofosbuvir and the at least one matrix compound, wherein in the adsorption-desorption isotherm of the at least one pharmaceutically acceptable matrix compound, the mass difference Δm (desorption) at 75% relative humidity and 25° C. is greater than or equal to the mass difference Δm (adsorption) at 75% relative humidity and 25° C. determined according to dynamic vapor sorption measurement, wherein the at least one matrix compound is selected from the group consisting of hydrophilic water-soluble polymers, silicon-based inorganic adsorbents and a combination of two or more thereof and wherein the weight ratio of the sofosbuvir and the matrix compound is from 6:4 to 8.5:1.5.

12. A process for the preparation of a solid composition, comprising sofosbuvir according to formula (I)

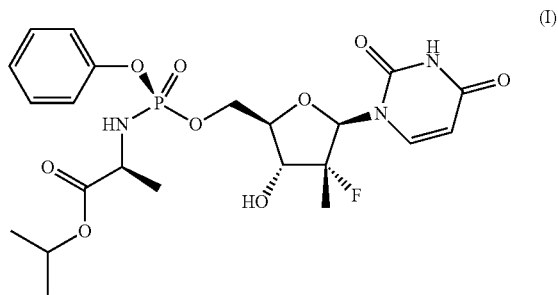 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

and at least one pharmaceutically acceptable matrix compound, said process comprising embedding sofosbuvir in a matrix consisting of the at least one pharmaceutically acceptable matrix compound by melting the at least one pharmaceutically acceptable matrix compound in solid form together with the sofosbuvir in solid form, wherein at least 99 weight-% of the sofosbuvir comprised in the composition are present in amorphous form, at least 99 weight-% of the solid composition consist of the sofosbuvir and the at least one matrix compound, and wherein the solid composition contains the sofosbuvir in an amount of at least 55 weight-% based on the combined weight of the sofosbuvir and the at least one matrix compound, wherein in the adsorption-desorption isotherm of the at least one pharmaceutically acceptable matrix compound, the mass difference Δm (desorption) at 75% relative humidity and 25° C. is greater than or equal to the mass difference Δm (adsorption) at 75% relative humidity and 25° C. determined according to dynamic vapor sorption measurement, wherein the at least one matrix compound is selected from the group consisting of hydrophilic water-soluble polymers, silicon-based inorganic adsorbents and a combination of two or more thereof, and wherein the weight ratio of the sofosbuvir and the matrix compound is from 6:4 to 8.5:1.5.

13. The process of claim 11, wherein the at least one solvent is selected from the group consisting of water, an organic solvent, and a combination of two or more thereof.

14. The process of claim 11, wherein the at least one matrix compound is selected from the group consisting of hydrophilic water-soluble polymers and a combination of two or more thereof and wherein the embedding comprises preparing a solution of the sofosbuvir and the at least one matrix compound in at least one solvent.

15. The process of claim 11, wherein the at least one matrix compound is selected from the group consisting of silicon-based inorganic adsorbents and a combination of two or more thereof and wherein the embedding comprises dispersing the at least one matrix compound in the solution.

16. The process of claim 11, wherein the solution of the sofosbuvir in at least one solvent is prepared from sofosbuvir of which at least 95 weight-% are present in its amorphous form, wherein the sofosbuvir is preferably prepared by a method comprising (i) providing sofosbuvir in at least one crystalline form or in amorphous form or as a mixture of at least one crystalline form and amorphous form;

(ii) dissolving at least a portion of the sofosbuvir provided according to (i) in at least one solvent, obtaining a solution comprising the sofosbuvir;

(iii) subjecting at least a portion of the solution obtained according to (ii) to lyophilization or rapid-drying, obtaining the sofosbuvir of which at least 95 weight-% are present in its amorphous form.

17. A process for the preparation of a pharmaceutical composition, said process comprising (a) providing a solid composition according to claim 1;
(b) admixing the solid composition provided according to (a) with at least one pharmaceutically acceptable excipient.

18. A solid composition, obtainable or obtained by a process according to claim 11.

19. A pharmaceutical composition, obtainable or obtained by a process according to claim 17.

20. A method for treating hepatitis C comprising administering a solid composition according to claim 1 to a human patient in need thereof.

* * * * *